(12) United States Patent
De Bethune et al.

(10) Patent No.: US 7,429,677 B2
(45) Date of Patent: Sep. 30, 2008

(54) SMALL MOLECULE ENTRY INHIBITORS

(75) Inventors: Marie-Pierre T. M. M. G De Bethune, Everberg (BE); Sandra De Meyer, Beerse (BE); Kurt Hertogs, Antwerp (BE); Rong Jian Lu, Chapel Hill, NC (US); Lieve Emma Jan Michiels, Mol (BE); Abdellah Tahri, Anderlecht (BE); Dong Xie, Germantown, MD (US); Michael Eissenstat, Frederick, MD (US)

(73) Assignee: Tibotec Pharmaceuticals Ltd., County Cork (IE)

( * ) Notice: Subject to any disclaimer, the term of this patent is extended or adjusted under 35 U.S.C. 154(b) by 101 days.

(21) Appl. No.: 10/507,180

(22) PCT Filed: Mar. 11, 2003

(86) PCT No.: PCT/EP03/50055

§ 371 (c)(1),
(2), (4) Date: Aug. 3, 2005

(87) PCT Pub. No.: WO03/075907

PCT Pub. Date: Sep. 18, 2003

(65) Prior Publication Data

US 2006/0025594 A1    Feb. 2, 2006

(30) Foreign Application Priority Data

Mar. 11, 2002   (EP)   ................ 02075998

(51) Int. Cl.
| C07C 315/00 | (2006.01) |
| C07C 317/00 | (2006.01) |
| C07C 321/00 | (2006.01) |
| C07C 323/00 | (2006.01) |
| C07C 381/00 | (2006.01) |

(52) U.S. Cl. ..................... 562/430; 562/432
(58) Field of Classification Search .......... 562/430, 562/432
See application file for complete search history.

(56) References Cited

U.S. PATENT DOCUMENTS 5,571,921 A * 11/1996 Bender et al. ............ 546/199

FOREIGN PATENT DOCUMENTS

| EP | 0 628 555 A1 | 12/1994 |
| FR | 1.557.887 | 1/1968 |
| WO | WO 91/05761 A1 | 5/1991 |
| WO | WO 95/05170 A1 | 2/1995 |
| WO | WO 03/004458 A1 | 1/2003 |

OTHER PUBLICATIONS

M. Hasegawa, et al., "Novel Napthalene Derivatives as Inhibitors of Human Immunoglobulin E Antibody Production", J. Med. Chem. (1997), 40, pp. 395-407.

J. Matysiak, et al., "In vitro inhibition properties of a new group of thiobenzanilides in relation to yeasts", European Journal of Pharmaceutical Sciences 10 (2000) 119-123.

J. Milton, et al., "Biaryl Acids: Novel Non-Nucleoside Inhibitors of HIV Reverse Transcriptase Types 1 and 2", Bioorganic & Medicinal Chemistry Letters 8 (1998) pp. 2623-2628.

V.B. Oza, et al., "Synthesis and Evaluation of Anthranilic Acid-Based Transthyretin Amyloid Fibril Inhibitors", Bioorganic & Medicinal Chemistry Letters 9 (1999) pp. 1-6.

A. Varnavas, et al., "Anthranoyl-anthranilic acid: a template for the development of a new class of cholecystokinin receptor ligands", Pharmazie 51 (1996) pp. 697-700.

* cited by examiner

*Primary Examiner*—Yvonne Eyler
*Assistant Examiner*—Jennifer Y Cho

(57) ABSTRACT

The present invention concerns a compound having the formula (I)

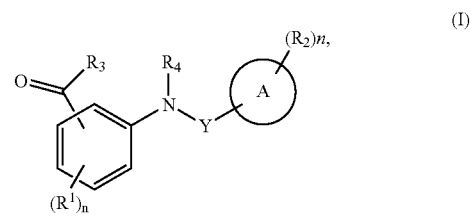

a N-oxide form, a stereochemical isomer, racemic mixture, salt, prodrug, ester or metabolite thereof. It further relates to processes for their preparation as well as pharmaceutical compositions, their use as medicines, and diagnostic kits comprising them. The present invention also concerns combinations of the present entry inhibitors with anti-retroviral agents. It further relates to their use in assays as reference compounds or as reagents. The compounds of the present invention are useful for preventing or treating infection by HIV and for treating AIDS.

4 Claims, No Drawings

SMALL MOLECULE ENTRY INHIBITORS

RELATED APPLICATIONS

This Application is a National Stage Application under 35 U.S.C. § 371 of PCT/EP03/50055, filed Mar. 11, 2003, which claims priority benefit of EP 02075998.1, filed on Mar. 11, 2002, both of which are incorporated herein by reference in their entirety.

The present invention relates to small molecules as entry inhibitors of a virus, such as HIV, processes for their preparation as well as pharmaceutical compositions, their use as medicines, and diagnostic kits comprising them. The present invention also concerns combinations of the present entry inhibitors with anti-retroviral agents. It further relates to their use in assays as reference compounds or as reagents. The compounds of the present invention are useful for preventing or treating infection by HIV and for treating AIDS.

The number of people living with HIV/AIDS totaled in December 2001 about 40 million of which more than 37 million adults and about 2.7 million children under 15 years old. The people newly infected with HIV in 2001 alone rose to 5 million whereas there were in 2001 3 million AIDS deaths. Current chemotherapy for these people infected with HIV/AIDS employs the inhibitors of the viral reverse transcriptase (RT) and protease enzymes. In view of the emergence of HIV strains resistant to the current generation of RT and protease inhibitors, there exists an increasing need for the development of new antivirals with novel mechanisms of action.

One of the new areas of emerging antiretrovirals is the area of the "entry inhibitors". These drugs are designed to block HIV from entering the human cell by interfering with various phases of attachment and fusion between HIV and the cell. The entry process can be divided in three sequentially distinct steps (1) binding of the virus envelope protein gp120 to the CD4 receptor on the host cell, (2) binding of the virus envelope protein gp120 to the co-receptors (CXCR4/CCR5) on the host cell, and (3) fusion of the virus and the host cell membranes, mediated by the virus envelope protein gp41.

Several (co)receptor inhibitors and two fusion inhibitors, T20 and T1249 (Trimeris, Durham, N.C., USA), peptides based on elements of gp41, are currently in the final stages of clinical development. The successful proof-of-principle studies conducted with T20 made that HIV fusion has been validated as a clinically relevant target.

However, the use of peptides has many drawbacks when they are to be developed as pharmaceutically acceptable drugs. Therefore, there is a need to develop small molecules which may block HIV from entering the human cell by interfering with various phases of attachment and fusion between HIV and the cell.

WO0004903, concerns a method of inhibiting HIV-1 infection comprising administering to a patient specific tetrazol derivates having a molecular weight of between 200 and 650 daltons and which inhibit the binding of gp120 to CD4.

Patent FR1557887 discloses diamide-diacids and derivatives, polymers for films and flexible coatings. Ponomarev et al., 1992, disclose the synthesis, structure and properties of ladder-type polyquinazolones. WO0164643 relates to benzamides and related inhibitors of factor XA, for coagulation disorders.

DETAILED DESCRIPTION OF THE INVENTION

It was found that the compounds of the present invention are inhibitors of the entry process of the HIV virus into the host cell. Said compounds having the formula (I),

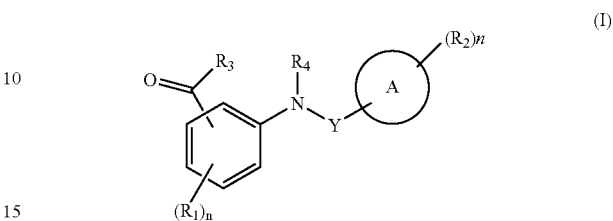

their N-oxide forms, stereochemical isomers, racemic mixtures, salts, prodrugs, esters and metabolites thereof, wherein A is aryl, heteroaryl or heterocycloalkyl;

$R^1$ represents hydrogen, halogen, hydroxy, amino, nitro, alkyl, alkyloxy, or a radical of formula (II),

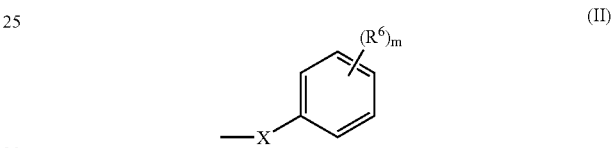

$R^2$ represents alkyl, alkenyl, alkynyl, hydroxy, halogen, nitro, cyano, amino, haloalkyl, cycloalkyl, aryl, heteroaryl, heterocycloalkyl, $R^8$—O—, $R^8$—S—, $R^8$—S(=O)$_2$—, $R^8$—C(=O)—, $R^8$—C(=S)—, $R^8$—C(=NH)—, $R^8$—C(=NCN)—, $R^8$—NH—, $(R^8)_2$—N—, HO—C(=O)—, NH$_2$—C(=O)—, NH$_2$—S(=O)$_2$—, NH$_2$—C(=S)—, NH$_2$—C(=NH)—, NH$_2$—C(=NCN)—, $R^8$—NR$^4$—C(=O)—, $R^8$—NR$^4$—S(=O)$_2$—, $R^8$—O—C(=O)—, $R^8$—C(=O)—NR$^4$—, $R^8$—S(=O)$_2$—NR$^4$—, $R^8$—C(=O)—O—, $R^8$—S—CH$_2$— or $R^8$—O—CH$_2$—C(=O)—;

$R^3$ represents hydroxy, amino, alkyloxy, cycloalkyloxy or mono- or disubstituted amino whereby the substituents can be selected from alkyl and cycloalkyl;

$R^4$ represents hydrogen, alkyl or cycloalkyl;

$R^6$ is hydrogen, amino, $R^7$—C(=O)—, $R^8$—S(=O)$_2$—NH—, $R^8$—C(=O)—NH—, $R^8$—C(=S)—NH—, $R^8$—C(=NH)—NH—, $R^8$—C(=NCN)—NH—, $R^8$—O—C(=O)—NH—, $R^8$—O-alkanediyl-C(=O)—NH—, $R^8$-alkanediyl-S(=O)$_2$—NH—, aryl-alkanediyl-C(=O)—NH—, aryl-alkenediyl-C(=O)—NH—, heteroaryl-alkanediyl-C(=O)—NH—, cycloalkyl-alkanediyl-C(=O)—NH—, heterocycloalkyl-alkanediyl-C(=O)—NH— or substituted alkyl whereby the substitutents can be selected from amino, $R^7$—C(=O)—, $R^8$—S(=O)$_2$—NH—, $R^8$—C(=O)—NH—, $R^8$—C(=S)—NH—, $R^8$—C(=NH)—NH—, $R^8$—C(=NCN)—NH—, $R^8$—O—C(=O)—NH—, $R^8$—O-alkanediyl-C(=O)—NH—, $R^8$-alkanediyl-S(=O)$_2$—NH—, aryl-alkanediyl-C(=O)—NH—, heteroaryl-alkanediyl-C(=O)—NH—, cycloalkyl-alkanediyl-C(=O)—NH— and heterocycloalkyl-alkanediyl-C(=O)—NH—;

$R^7$ represents hydroxy, amino, alkyloxy, cycloalkyloxy or mono- or disubstituted amino whereby the substituents can be selected from alkyl and cycloalkyl;

$R^8$ represents alkyl, haloalkyl, cycloalkyl, aryl, heteroaryl or heterocycloalkyl;

Y represents alkanediyl, —C(=O)—, —C(=S)—, —C(=NH)—, —C(=NCN)—, —S(=O)—, —S(=O)$_2$—, —C(=O)—CH$_2$—O—, —C(=O)—O—, —C(=O)—(CH$_2$)$_p$—, —C(=O)—NH— or -alkenediyl-C(=O)—;

X is a direct bond, —O—, —S—, —S(=O)$_2$—, —O—S(=O)$_2$—, —S(=O)$_2$—O—, —NH—S(=O)$_2$—, —S(=O)$_2$—NH—, —C(=O)—, —C(=S)—, —C(=NH)—, —C(=NCN)—, —O—C(=O)—, —C(=O)—O—, —NH—C(=O)—, —C(=O)—NH— or alkanediyl;

m and n are each independently zero, one or two;

p is an integer from 1 to 4.

The compounds of the present invention further encompass the formula (III),

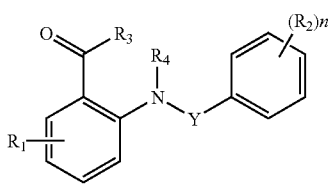

(III)

their N-oxide forms, stereochemical isomers, racemic mixtures, salts, prodrugs, esters and metabolites thereof, wherein $R^1$ represents hydrogen, halogen or a radical of formula (II),

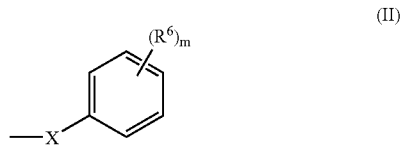

(II)

$R^2$ represents alkyl, alkenyl, alkynyl, hydroxy, halogen, nitro, cyano, amino, haloalkyl, cycloalkyl, aryl, heteroaryl, heterocycloalkyl, $R^8$—O—, $R^8$—S—, $R^8$—S(=O)$_2$—, $R^8$—C(=O)—, $R^8$—C(=S)—, $R^8$—C(=NH)—, $R^8$—C(=NCN)—, $R^8$—NH—, $(R^8)_2$—N—, HO—C(=O)—, NH$_2$—C(=O)—, NH$_2$—S(=O)$_2$—, NH$_2$—C(=S)—, NH$_2$—C(=NH)—, NH$_2$—C(=NCN)—, $R^8$—NR$^4$—C(=O)—, $R^8$—NR$^4$—S(=O)$_2$—, $R^8$—O—C(=O)—, $R^8$—C(=O)—NR$^8$—, $R^8$—S(=O)$_2$—NR$^4$— or $R^8$—C(=O)—O—;

$R^3$ represents hydroxy, amino, alkyloxy, cycloalkyloxy or mono- or disubstituted amino whereby the substituents can be selected from alkyl and cycloalkyl;

$R^4$ represents hydrogen, alkyl or cycloalkyl;

$R^6$ is hydrogen, amino, $R^7$—C(=O)—, $R^8$—S(=O)$_2$—NH—, $R^8$—C(=O)—NH—, $R^8$—C(=S)—NH—, $R^8$—C(=NH)—NH—, $R^8$—C(=NCN)—NH—, $R^8$—O—C(=O)—NH—, $R^8$—O-alkanediyl-C(=O)—NH—, $R^8$-alkanediyl-S(=O)$_2$—NH—, aryl-alkanediyl-C(=O)—NH—, heteroaryl-alkanediyl-C(=O)—NH—, cycloalkyl-alkanediyl-C(=O)—NH—, heterocycloalkyl-alkanediyl-C(=O)—NH— or substituted alkyl whereby the substitutents can be selected from amino, $R^7$—C(=O)—, $R^8$—S(=O)$_2$—NH—, $R^8$—C(=O)—NH—, $R^8$—C(=S)—NH—, $R^8$—C(=NH)—NH—, $R^8$—C(=NCN)—NH—, $R^8$—O—C(=O)—NH—, $R^8$—O-alkanediyl-C(=O)—NH—, $R^8$-alkanediyl-S(=O)$_2$—NH—, aryl-alkanediyl-C(=O)—NH—, heteroaryl-alkanediyl-C(=O)—NH—, cycloalkyl-alkanediyl-C(=O)—NH— and heterocycloalkyl-alkanediyl-C(=O)—NH—;

$R^7$ represents hydroxy, amino, alkyloxy, cycloalkyloxy or mono- or disubstituted amino whereby the substituents can be selected from alkyl and cycloalkyl;

$R^8$ represents alkyl, cycloalkyl, aryl, heteroaryl or heterocycloalkyl;

Y represents alkanediyl, —C(=O)—, —C(=S)—, —C(=NH)—, —C(=NCN)—, —S(=O)—, —S(=O)$_2$—, —C(=O)—CH$_2$—O—, —C(=O)—O—, —C(=O)—(CH$_2$)$_p$—;

X is a direct bond, —O—, —S—, —S(=O)$_2$—, —O—S(=O)$_2$—, —S(=O)$_2$—O—, —NH—S(=O)$_2$—, —S(=O)$_2$—NH—, —C(=O)—, —C(=S)—, —C(=NH)—, —C(=NCN)—, —O—C(=O)—, —C(=O)—O—, —NH—C(=O)—, —C(=O)—NH— or alkanediyl;

m and n are each independently zero, one or two;

p is an integer from 1 to 4.

This invention also concerns the quaternization of the nitrogen atoms of the present compounds. A basic nitrogen can be quaternized with any agent known to those of ordinary skill in the art including, for instance, lower alkyl halides, dialkyl sulfates, long chain halides and arylalkyl halides.

As used herein, the term "halo" or "halogen" as a group or part of a group is generic for fluoro, chloro, bromo or iodo.

The term "alkyl", alone or in combination, means straight and branched chained saturated hydrocarbon radicals containing from 1 to 10 carbon atoms, preferably from 1 to 8 carbon atoms, more preferably from 1 to 6 carbon atoms, and even more preferably from 1 to 4 carbon atoms. Examples of such alkyl radicals include methyl, ethyl, n-propyl, isopropyl, n-butyl, isobutyl, sec-butyl, tert-butyl, 2-methylbutyl, pentyl, iso-amyl, hexyl, 3-methylpentyl, octyl and the like.

The term "alkanediyl", alone or in combination, defines bivalent straight and branched chained saturated hydrocarbon radicals containing from 1 to 10 carbon atoms, preferably from 1 to 8 carbon atoms, more preferably from 1 to 6 carbon atoms and even more preferably from 1 to 4 carbon atoms, such as, for example, methylene, ethan-1,2-diyl, propan-1,3-diyl, propan-1,2-diyl, butan-1,4-diyl, pentan-1,5-diyl, hexan-1,6-diyl, 2-methylbutan-1,4-diyl, 3-methylpentan-1,5-diyl and the like.

The term "alkenediyl", alone or in combination, defines bivalent straight and branched chained hydrocarbon radicals containing from 2 to 10 carbon atoms, preferably from 2 to 8 carbon atoms, more preferably from 2 to 6 carbon atoms and even more preferably from 2 to 4 carbon atoms, containing at least one double bond such as, for example, ethen-1,2-diyl, propen-1,3-diyl, propen-1,2-diyl, buten-1,4-diyl, penten-1,5-diyl, hexen-1,6-diyl, 2-methylbuten-1,4-diyl, 3-methylpenten-1,5-diyl and the like.

The term "alkenyl", alone or in combination, defines straight and branched chained hydrocarbon radicals containing from 2 to about 18 carbon atoms, preferably from 2 to 8 carbon atoms, more preferably from 2 to 6 carbon atoms and even more preferably from 2 to 4 carbon atoms, containing at least one double bond such as, for example, ethenyl, propenyl, butenyl, pentenyl, hexenyl and the like.

The term "alkynyl", alone or in combination, defines straight and branched chained hydrocarbon radicals having from 2 to 10 carbon atoms, more preferably from 2 to about 6 carbon atoms and even more preferably from 2 to 4 carbon atoms, containing at least one triple bond. Examples of alkynyl radicals include ethynyl, propynyl, propargyl, butynyl, pentynyl, hexynyl and the like.

The term "cycloalkyl" alone or in combination, means a saturated or partially unsaturated monocyclic, bicyclic or polycyclic alkyl radical wherein each cyclic moiety contains from about 3 to about 8 carbon atoms, more preferably from about 3 to about 7 carbon atoms, even more preferably from about 5 to 7 carbon atoms. Examples of monocyclic cycloalkyl radicals include cyclopropyl, cyclobutyl, cyclopentyl, cyclohexyl, cycloheptyl, cyclooctyl and the like. Examples of polycyclic cycloalkyl radicals include decahydronaphthyl, bicyclo [5.4.0] undecyl, adamantyl, and the like.

The term "aryl" alone or in combination, is meant to include mono-, bi-, and tricyclic aromatic carbocycles such as phenyl, naphtyl, which may be optionally substituted with one or more substituents independently selected from alkyl, alkenyl, alkynyl, hydroxy, halogen, nitro, cyano, amino, cycloalkyl, haloalkyl, heteroaryl, heterocycloalkyl, $R^9$—O—, $R^9$—S—, $R^9$—S(=O)$_2$—, $R^9$C(=O)—, $R^9$—C(=S)—, $R^9$—C(=NH)—, $R^9$—C(=NCN)—, $R^9$—NH—, $(R^9)_2$—N—, HO—C(=O)—, NH$_2$—C(=O)—, NH$_2$—S(=O)$_2$—, NH$_2$—C(=S)—, NH$_2$—C(=NH)—, NH$_2$—C(=NCN)—, $R^9$—NR$^4$—C(=O)—, $R^9$—NR$^4$—S(=O)$_2$—, $R^9$—O—C(=O)—, $R^9$—C(=O)—NR$^4$—, $R^9$—S(=O)$_2$—NR$^4$—, $R^9$—C(=O)—O— and phenyl optionally substituted with one or more substituents selected from alkyl, alkyloxy, halogen, hydroxy, optionally mono- or disubstituted amino, nitro, cyano, haloalkyl, carboxyl, alkyloxycarbonyl, cycloalkyl, heterocycloalkyl, optionally mono- or disubstituted aminocarbonyl, alkylthio and alkylsulfonyl; whereby the optional substituents on any amino function are independently selected from alkyl, alkyloxy, heterocycloalkyl, heterocycloalkyl-alkanediyl, heterocycloalkyloxy, heterocycloalkyloxy-alkanediyl, phenyl, phenyloxy, phenyloxyalkanediyl, phenyl-alkanediyl, alkyloxycarbonylamino, amino, and amino-alkanediyl, whereby each of the latter amino groups may optionally be mono- or where possible di-substituted with alkyl.

Examples of aryl includes phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl and the like.

Wherever used, unless specified otherwise, the variable $R^9$ represents alkyl, haloalkyl, cycloalkyl, heteroaryl, heterocycloalkyl or phenyl optionally substituted with one or more substituents selected from alkyl, alkyloxy, halogen, hydroxy, optionally mono- or disubstituted amino, nitro, cyano, haloalkyl, carboxyl, alkyloxycarbonyl, cycloalkyl, heterocycloalkyl, optionally mono- or disubstituted aminocarbonyl, alkylthio and alkylsulfonyl; whereby the optional substituents on any amino function are independently selected from alkyl, alkyloxy, heterocycloalkyl, heterocycloalkyl-alkanediyl, heterocycloalkyloxy, heterocycloalkyloxy-alkanediyl, phenyl, phenyloxy, phenyloxy-alkanediyl, phenyl-alkanediyl, alkyloxycarbonylamino, amino, and amino-alkanediyl, whereby each of the latter amino groups may optionally be mono- or where possible di-substituted with alkyl.

The term "haloalkyl" alone or in combination, means an alkyl radical having the meaning as defined above wherein one or more hydrogens are replaced with a halogen, preferably, chloro or fluoro atoms, more preferably fluoro atoms. Examples of such haloalkyl radicals include chloromethyl, 1-bromoethyl, fluoromethyl, difluoromethyl, trifluoromethyl, 1,1,1-trifluoroethyl and the like.

The term "heteroaryl" alone or in combination, means an aromatic monocyclic, bicyclic or tricyclic heterocycle having from 5 to 14 ring members, preferably from 5 to 10 ring members and more preferably from 5 to 6 ring members, which contains one or more heteroatom ring members selected from nitrogen, oxygen and sulphur and which is optionally substituted on one or more carbon atoms by halogen, hydroxy, nitro, cyano, alkyl, haloalkyl, alkyloxy, aminoalkanediyl, optionally mono- or disubstituted amino, carboxyl, alkyloxycarbonyl, cycloalkyl, optionally mono- or disubstituted aminocarbonyl, methylthio, methylsulfonyl, aryl, heterocycloalkyl, and an aromatic monocyclic, bicyclic or tricyclic heterocycle having from 5 to 12 ring members; whereby the optional substituents on any amino function are independently selected from alkyl, alkyloxy, heterocycloalkyl, heterocycloalkyl-alkanediyl, heterocycloalkyloxy, heterocycloalkyloxy-alkanediyl, aryl, aryloxy, aryloxyalkanediyl, arylalkanediyl, alkyloxycarbonylamino, amino, and aminoalkanediyl; whereby each of the latter amino groups may optionally be mono- or where possible di-substituted with alkyl.

The term "heterocycloalkyl" alone or in combination, means a saturated or partially unsaturated monocyclic, bicyclic or tricyclic heterocycle having from 3 to 14 ring members, preferably from 5 to 10 ring members and more preferably from 5 to 6 ring members, which contains one or more heteroatom ring members selected from nitrogen, oxygen and sulphur and which is optionally substituted on one or more carbon atoms by alkyl, alkyloxy, halogen, hydroxy, oxo, optionally mono- or disubstituted amino, optionally mono- or di substituted amino-alkanediyl, nitro, cyano, haloalkyl, carboxyl, alkyloxycarbonyl, cycloalkyl, optionally mono- or disubstituted aminocarbonyl, methylthio, methylsulfonyl, aryl and a saturated or partially unsaturated monocyclic, bicyclic or tricyclic heterocycle having from 3 to 14 ring members; whereby the optional substituents on any amino function are independently selected from alkyl, alkyloxy, heteroaryl, heteroaryl-alkanediyl, heteroaryloxy, heteroaryloxy-alkanediyl, aryl, aryloxy, aryloxy-alkanediyl, aryl-alkanediyl, alkyloxycarbonylamino, amino, and amino-alkanediyl; whereby each of the latter amino groups may optionally be mono- or where possible di-substituted with alkyl.

The term "alkyloxy" alone or in combination, is defined as an alkyl group attached to an oxygen atom, wherein the alkyl is a straight and branched chained saturated hydrocarbon radical having from 1 to 10 carbon atoms, more preferably from 2 to 6 carbon atoms, such as the groups methoxy, ethoxy, propoxy, butoxy, pentyloxy, hexyloxy, 2-methylbutyloxy, 3-methylpentyloxy and the like.

The term "cycloalkyloxy" alone or in combination, is defined as a cycloalkyl group attached to an oxygen atom, wherein the cycloalkyl is a saturated or partially unsaturated monocyclic, bicyclic or polycyclic alkyl radical, wherein each cyclic moiety contains from about 3 to about 8 carbon atoms, more preferably from about 3 to about 7 carbon atoms. Examples of monocyclic cycloalkyloxy radicals include cyclopropyloxy, cyclobutyloxy, cyclopentyloxy, cyclohexyloxy, cycloheptyloxy, cyclooctyloxy and the like.

As used herein, the term $C(=O)$ is meant to define a carbonyl moiety, the term $C(=S)$ is meant to define a thiocarbonyl moiety, the term $S(=O)$ is meant to define a sulfoxyl or sulfinyl moiety, the term $S(=O)_2$ is meant to define a sulfonyl moiety, the term $C(=NH)$ is meant to define an imino moiety and the term $C(=NCN)$ is meant to define a cyanoimino moiety.

As used herein, the term hydroxy means —OH, the term nitro means —$NO_2$, the term cyano means —CN, the term thio means —S, the term oxo means =O.

Whenever the terms "one or more substituents" or "substituted" are used in defining the compounds of formula (I), (II) and (III), it is meant to indicate that one or more hydrogens on the atom indicated in the expressions using "one or more substituents" or "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

When any variable (e.g. halogen or $C_{1-6}$alkyl) occurs more than one time in any constituent, each definition is independent.

The term "prodrug" as used throughout this text means the pharmacologically acceptable derivatives such as esters, amides and phosphates, such that the resulting in vivo biotransformation product of the derivative is the active drug as defined in the compounds of the present invention. The reference by Goodman and Gilman (The Pharmacological Basis of Therapeutics, $8^{th}$ ed, McGraw-Hill, Int. Ed. 1992, "Biotransformation of Drugs", pp 13-15) describing prodrugs generally is hereby incorporated. Prodrugs of a compound of the present invention are prepared by modifying functional groups present in the compound in such a way that the modifications are cleaved, either in routine manipulation or in vivo, to the parent compound. Prodrugs include compounds of the present invention wherein a hydroxy group, or an amino group is bonded to any group that, when the prodrug is administered to a patient, cleaves to form a free hydroxyl or free amino, respectively.

Prodrugs are characterized by excellent aqueous solubility, increased bioavailability and are readily metabolized into the active inhibitors in vivo.

For therapeutic use, the salts of the compounds of of the present invention are those wherein the counter-ion is pharmaceutically or physiologically acceptable. However, salts having a pharmaceutically unacceptable counter-ion may also find use, for example, in the preparation or purification of a pharmaceutically acceptable compound of the present invention. All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The compounds of the present invention containing an acidic proton may also be converted into their non-toxic metal or amine addition salt form by treatment with appropriate organic and inorganic bases. Appropriate base salt forms comprise, for example, the ammonium salts, quaternary ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms that the compounds of the present invention are able to form. Examples of such forms are e.g. hydrates, alcoholates and the like.

The N-oxide forms of the present compounds are meant to comprise the compounds wherein one or several nitrogen atoms are oxidized to the so-called N-oxide.

The present compounds may also exist in their tautomeric forms. Such forms, although not explicitly indicated in the above formula are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 80% of one isomer and maximum 20% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess and the diastereomeric excess respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of the present invention can be obtained separately by conventional methods. Appropriate physical separation methods which may advantageously be employed are, for example, selective crystallization and chromatography, e.g. column chromatography.

The compounds may contain one or more asymmetric centers and thus may exist as different stereoisomeric forms. The absolute configuration of each asymmetric center that may be present in the compounds may be indicated by the stereochemical descriptors R and S, this R and S notation corresponding to the rules described in Pure Appl. Chem. 1976, 45, 11-30.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

One group of compounds are those compounds where one or more of the following restrictions apply:

Y is —C(=O)—, or —S(=O)$_2$—;

$R^1$ is formula (II), $R^2$ is halogen, bromo, chloro, alkyl, haloalkyl, alkyloxy, alkenyl, or alkynyl, wherein said $R^2$ radicals are located in compound of formula (III), respective from the moiety Y, at meta, para, and meta and para positions;

n is 1;

X is —CH$_2$—, —NH—S(=O)$_2$—, —S(=O)$_2$—NH—, —NH—C(=O)—, or —C(=O)—NH—;

$R^6$ is $R^7$—C(=O)—, $R^8$—S(=O)$_2$—NH—, or $R^8$—C(=O)—NH—, wherein said $R^6$ radicals are located in compound of formula (H) adjacent to each other, i.e. at meta and para positions, or at ortho and meta positions, respective from the moiety X;

m is 2;

$R^7$ is hydroxy, or alkyloxy;

$R^8$ is aryl substituted with halogen, bromo, chloro, alkyl, alkyloxy haloalkyl, alkenyl, alkynyl, wherein said substituents on the aryl radical are located at meta or para positions, respective from the point of attachment of said aryl group.

In another embodiment, the compound of the present invention is a monomer, such as, and without being limited to, the example,

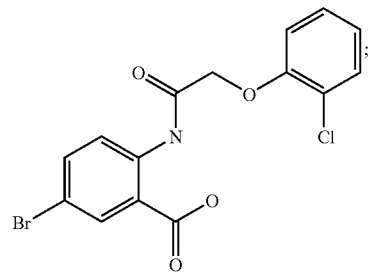

or a dimer such as, and without being limited to, the example,

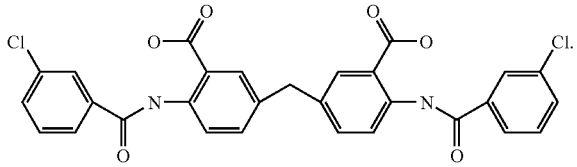

Particular reaction procedures to make the present compounds are described below in the schemes 1 to 4 and in the examples (schemes 5 and 6). In all the preparations further described, the reaction products may be isolated from the medium and, if necessary, further purified according to methodologies generally known in the art such as, for example, extraction, crystallization, trituration and chromatography.

Scheme 1

Compounds of type 1-A such as anthranilic acids are mixed with solvents, like THF, and a base such as K$_2$CO$_3$ or Na$_2$CO$_3$, solubilized in water, and followed by addition of compound 1-B to the previuos mixture. After several hours of stirring at room temperature, compound 1-C is formed. In order to get pure compound 1-C out from the solution, an acidification of the mixture and extraction with a solvent such as ethylacetate is applied. Compound 1-C is then reduced with for instance Pd/C and hydrogen in a solvent such as alcohols ethanol or methanol. This is followed by mixing at room temperature and removing solvent after filtration, from which compound 1-D is obtained. Compound 1-E is added and with the use of THF, K$_2$CO$_3$ or Na$_2$CO$_3$, and water, such as in the first step, we finally obtain compound 1-F.

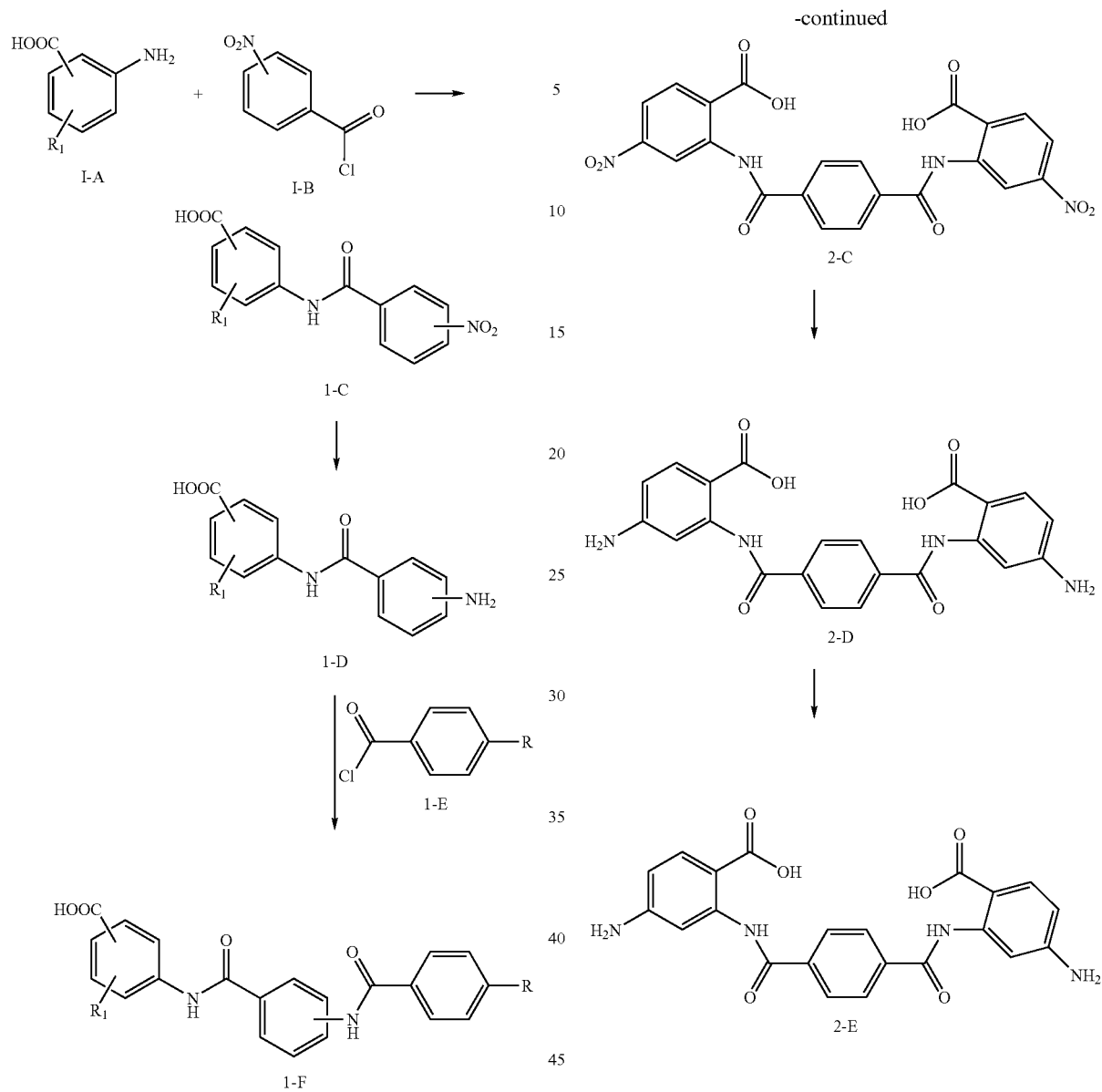
Schemes 2 and 3 below follow a similar execution strategy as in scheme 1.
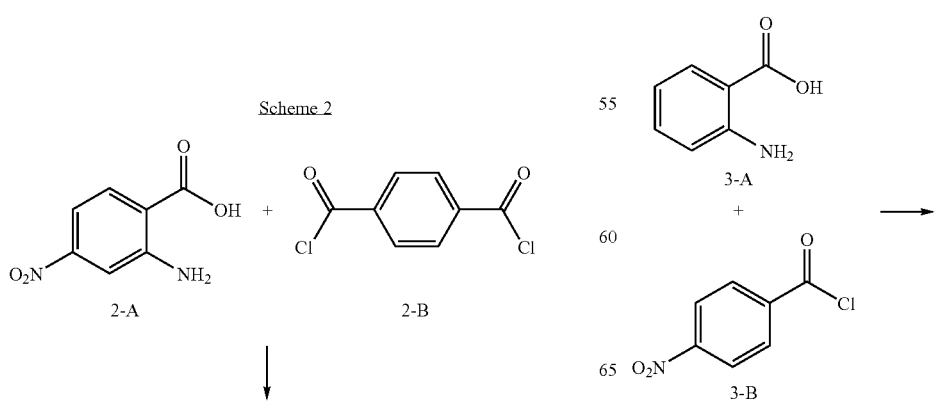

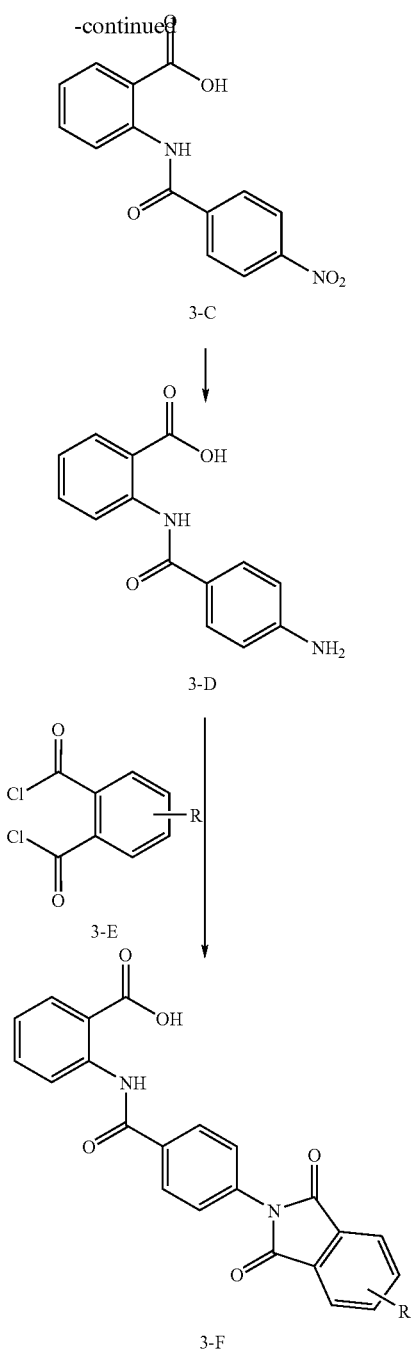

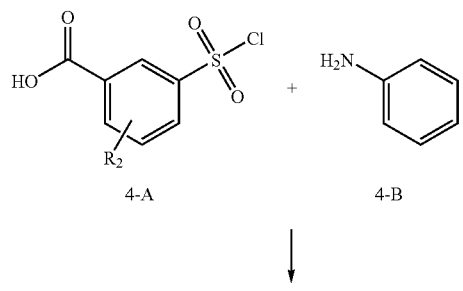

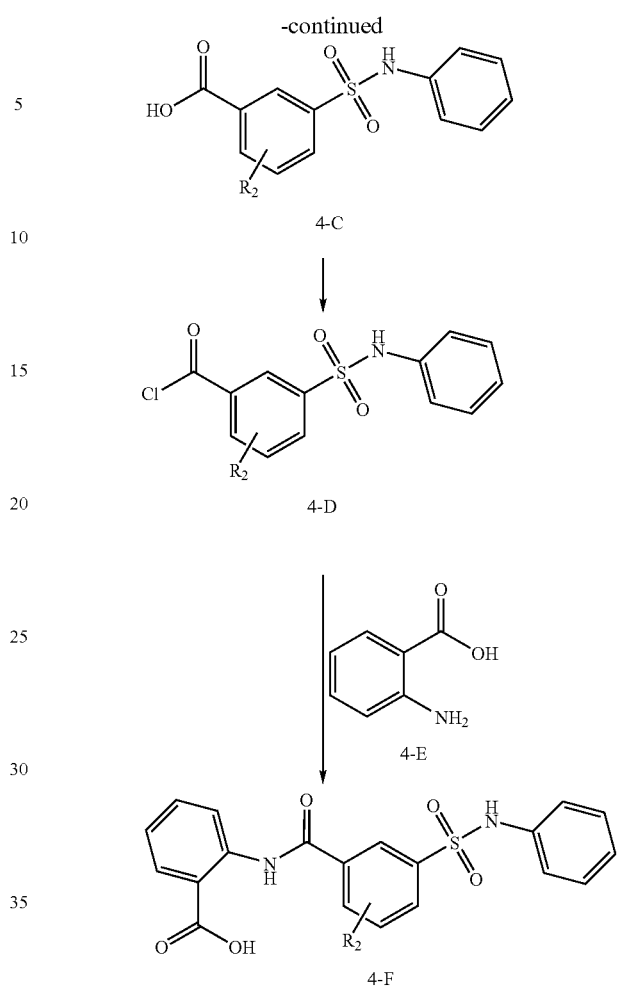

Compounds of type 4-A such as anthranilic acids are mixed with solvents, like THF, and a base such as $K_2CO_3$ or $Na_2CO_3$, solubilized in water, and followed by addition of compound 4-B to the previuos mixture. After several hours of stirring at room temperature, compound 4-C is formed. In order to get pure compound 4-C out from the solution, an acidification of the mixture and extraction with a solvent such as ethylacetate is applied. Compound 4-C is then refluxed in thionyl chloride for several hours. After removing the excess of thionyl chloride, water is added and compound 4-D is extracted with diclrolomethane. This is followed by removal of the solvent and mixing compound 4-D with compound 4-E, in the presence of solvents like THF, a base such as $K_2CO_3$ or $Na_2CO_3$, and water, thus finally obtaining compound 4-F.

The compounds of the present invention may also be converted to the corresponding N-oxide forms following art-known procedures for converting a trivalent nitrogen into its N-oxide form. Said N-oxidation reaction may generally be carried out by reacting the starting material of compounds with appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloro-benzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

In Table 1 below, there are listed a series of compounds according to the present invention. On the left column, there is indicated the synthesis scheme described in this invention, which allows their preparation. It is to be understood that this invention is not to be limited to the proposed preparation models. Further, the toxicity of the compounds has been measured on mock-infected cells by methods known to the skilled in the art. $CC_{50}$ values obtained are higher than 25 µM. The selectivity index is then calculated from the ratio between the toxicity values ($CC_{50}$ values) and the $EC_{50}$ values (effective drug concentration at which 50% of the viral population is inhibited) obtained from these compounds in a cellular assay.

TABLE I

| scheme | Compound of the present invention |
| --- | --- |

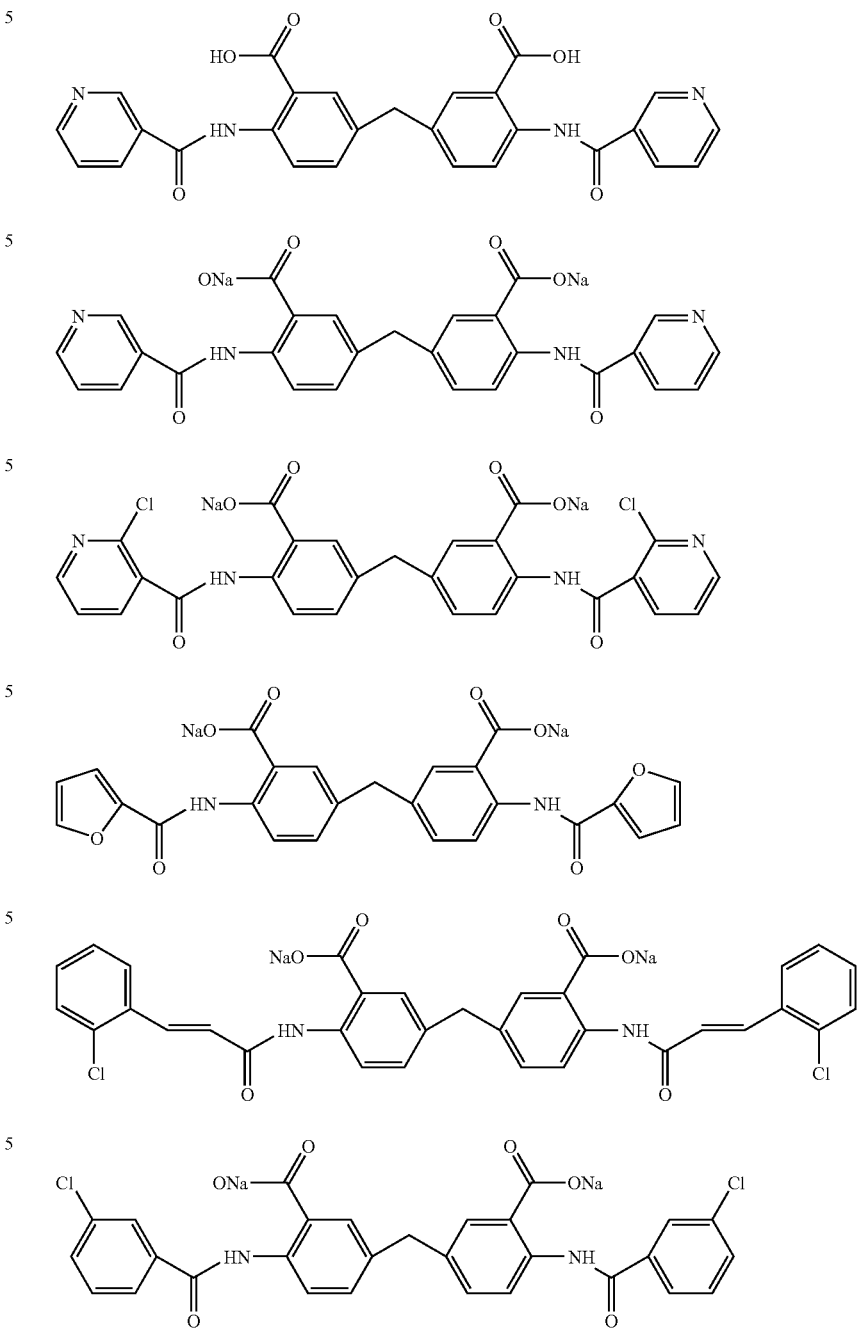

TABLE I-continued
| scheme | Compound of the present invention |
|---|---|
| 5 | 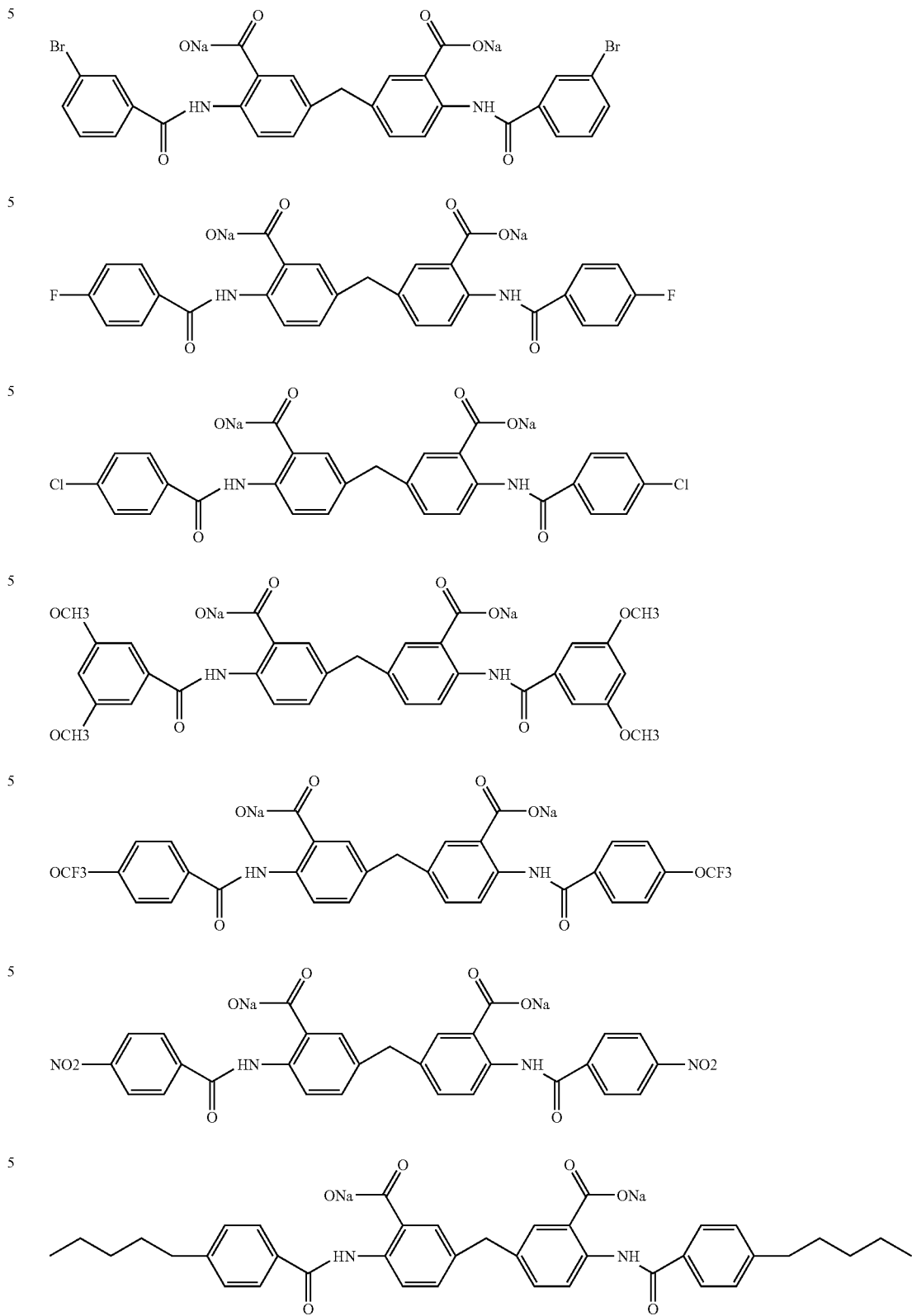 |
| 5 | |
| 5 | |
| 5 | |
| 5 | |
| 5 | |
| 5 | |

TABLE I-continued
| scheme | Compound of the present invention |
|---|---|
| 5 | 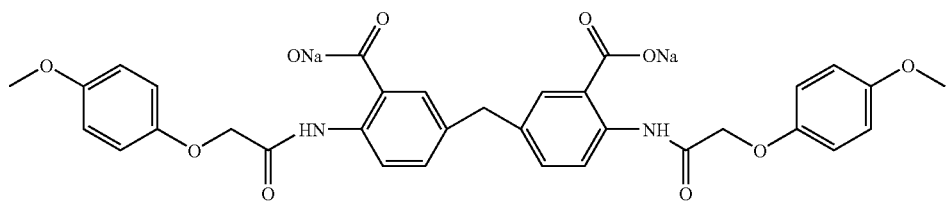 |
| 5 | 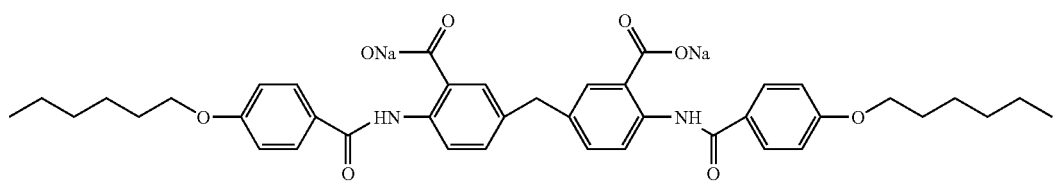 |
| 5 | 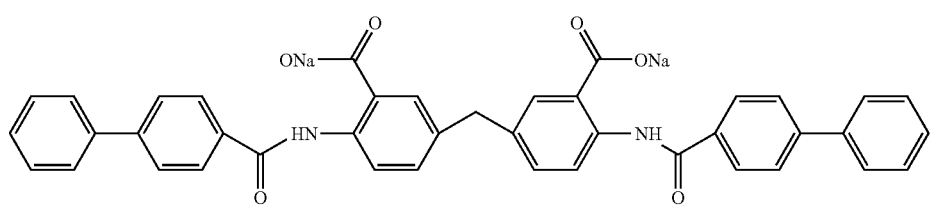 |
| 5 | 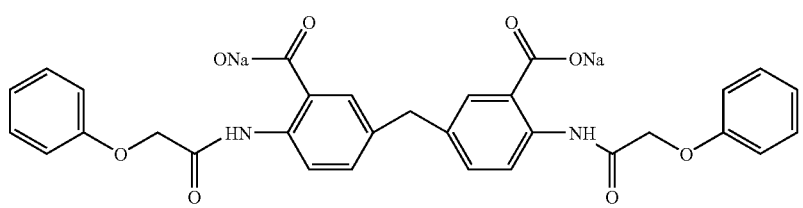 |
| 5 | 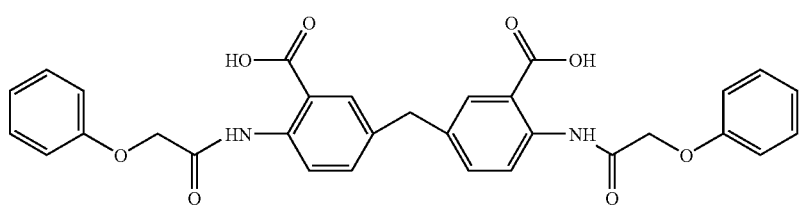 |
| 5 | 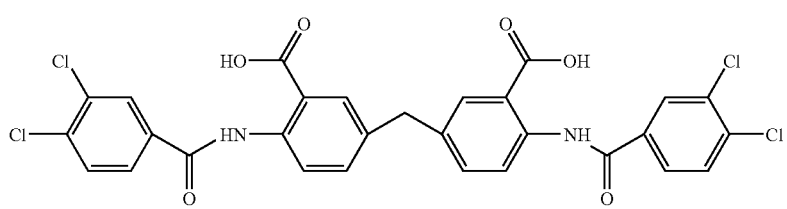 |
| 5 | 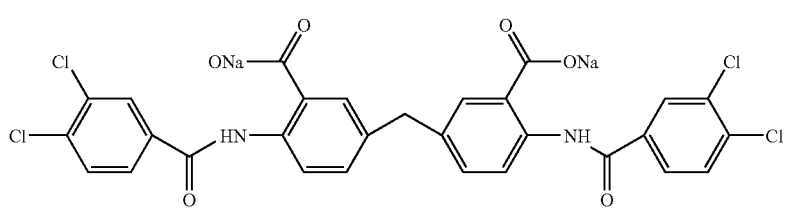 |

TABLE I-continued
| scheme | Compound of the present invention |
|---|---|
| 5 | 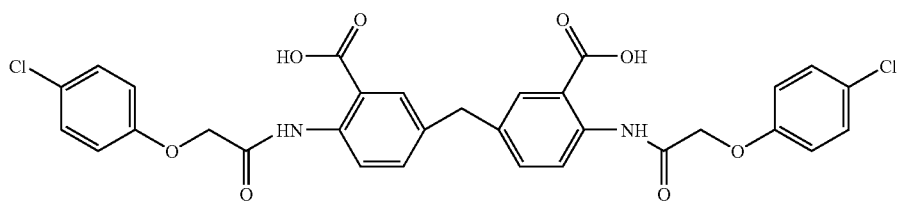 |
| 5 | 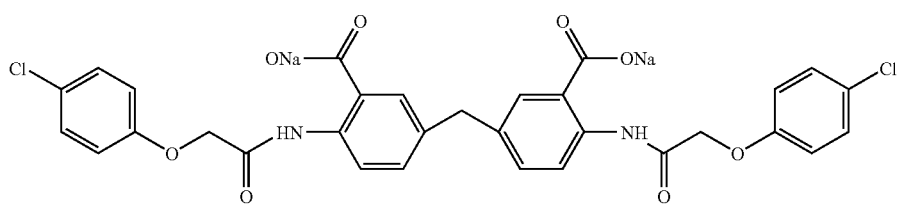 |
| 5 | 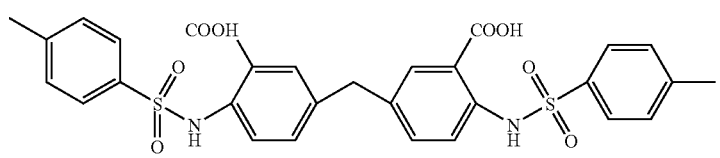 |
| 5 | 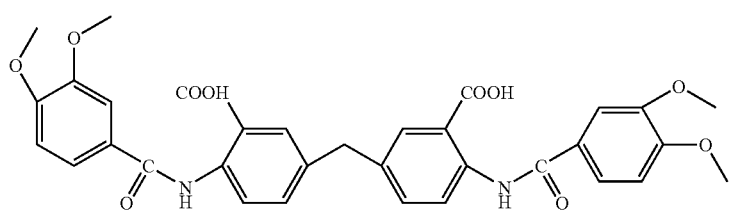 |
| 5 | 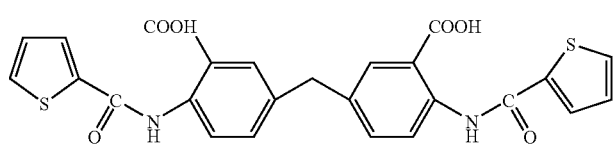 |
| 6 | 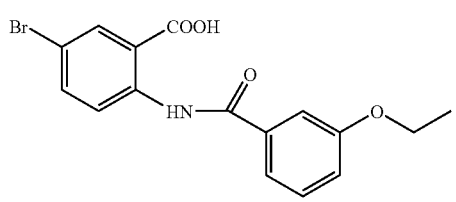 |
| 6 | 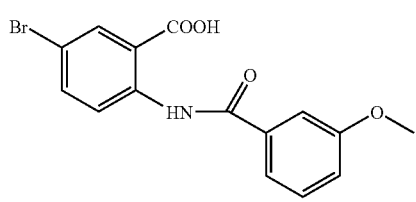 |
| 6 | 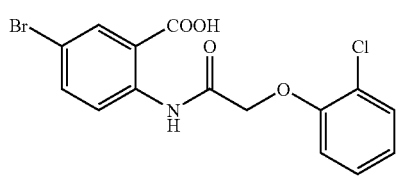 |

TABLE I-continued
| scheme | Compound of the present invention |
|---|---|
| 6 | 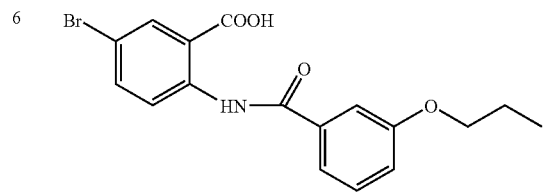 |
| 6 | 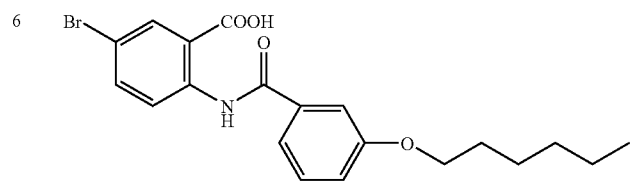 |
| 6 | 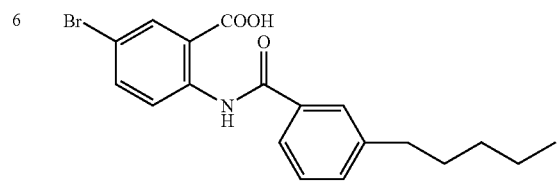 |
| 6 | 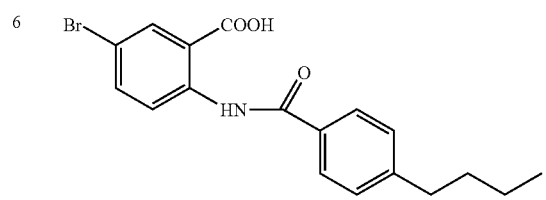 |
| 6 | 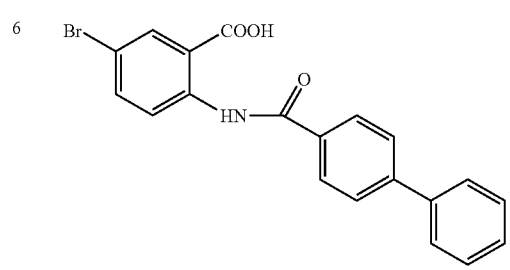 |
| 6 | 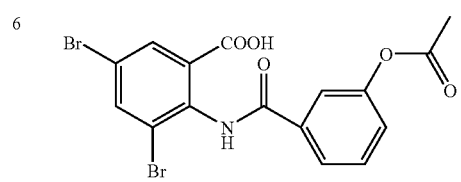 |
| 1 | 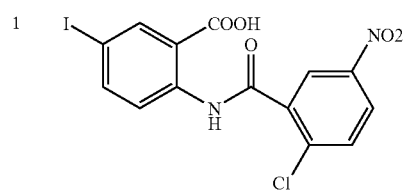 |
| 1 | 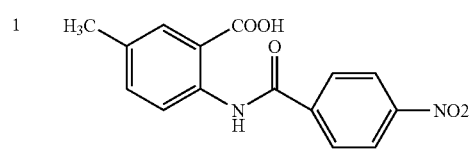 |

TABLE I-continued
| scheme | Compound of the present invention |
|---|---|
| 6 | |
| 1 | |
| 6 | |
| 6 | |
| 6 | |
| 6 | |
| 6 | |
| 6 | |
| 6 | |
| 6 | |
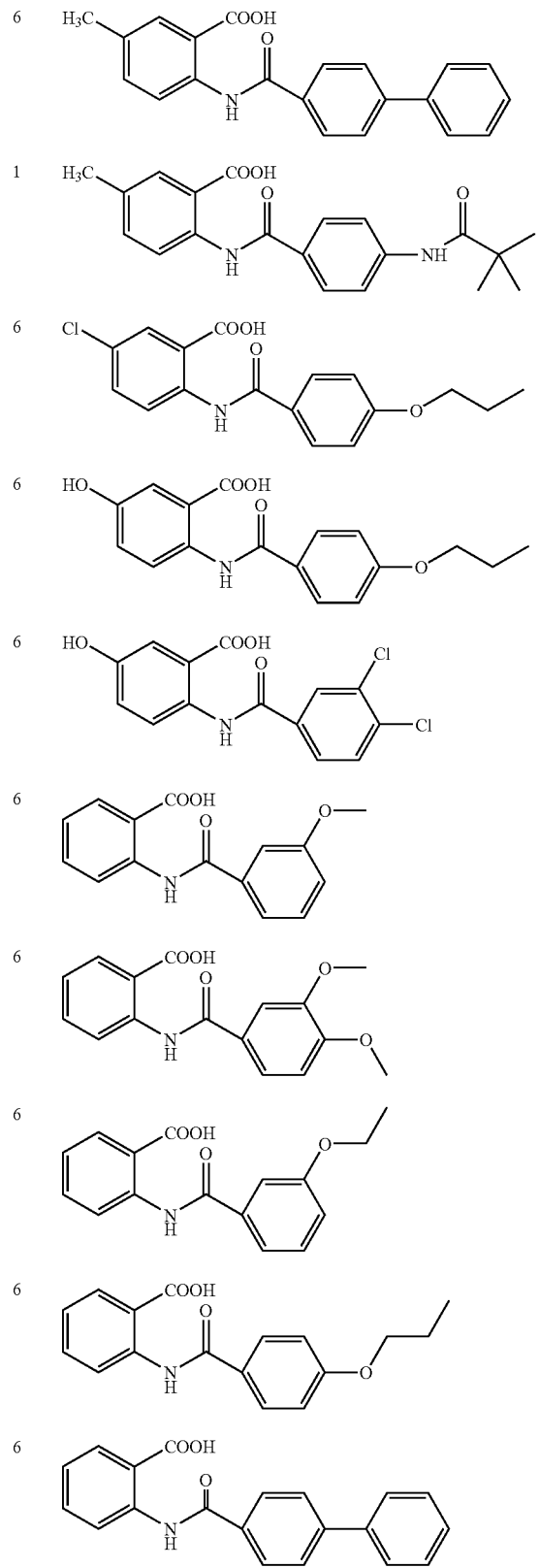

TABLE I-continued

| scheme | Compound of the present invention |
|---|---|
| 6 | 4-carboxyphenyl 4'-phenylbenzamide (4-HOOC-C6H4-NH-CO-C6H4-C6H5) |
| 6 | 3-carboxyphenyl 4'-phenylbenzamide |
| 1 | 2-carboxyphenyl-NH-CO-C6H4-NH-CO-C6H4-C6H5 |
| 1 | 4-bromo-2-carboxyphenyl-NH-CO-C6H4-NH-CO-C6H4-C6H5 |
| 1 | 2-carboxyphenyl-NH-CO-C6H4(3-NHCO-C6H4-C6H5) |
| 1 | 4-bromo-2-carboxyphenyl-NH-CO-C6H4(3-NHCO-C6H4-C6H5) |
| 1 | 2-carboxyphenyl-NH-CO-(5-NH2, 2-Cl-phenyl) |
| 6 | 2-carboxyphenyl-NH-CO-(3-OAc-phenyl) |
| 6 | 2-carboxyphenyl-NH-CO-(3-OC(O)CF3-phenyl) |

TABLE I-continued
| scheme | Compound of the present invention |
|---|---|
| 6 | 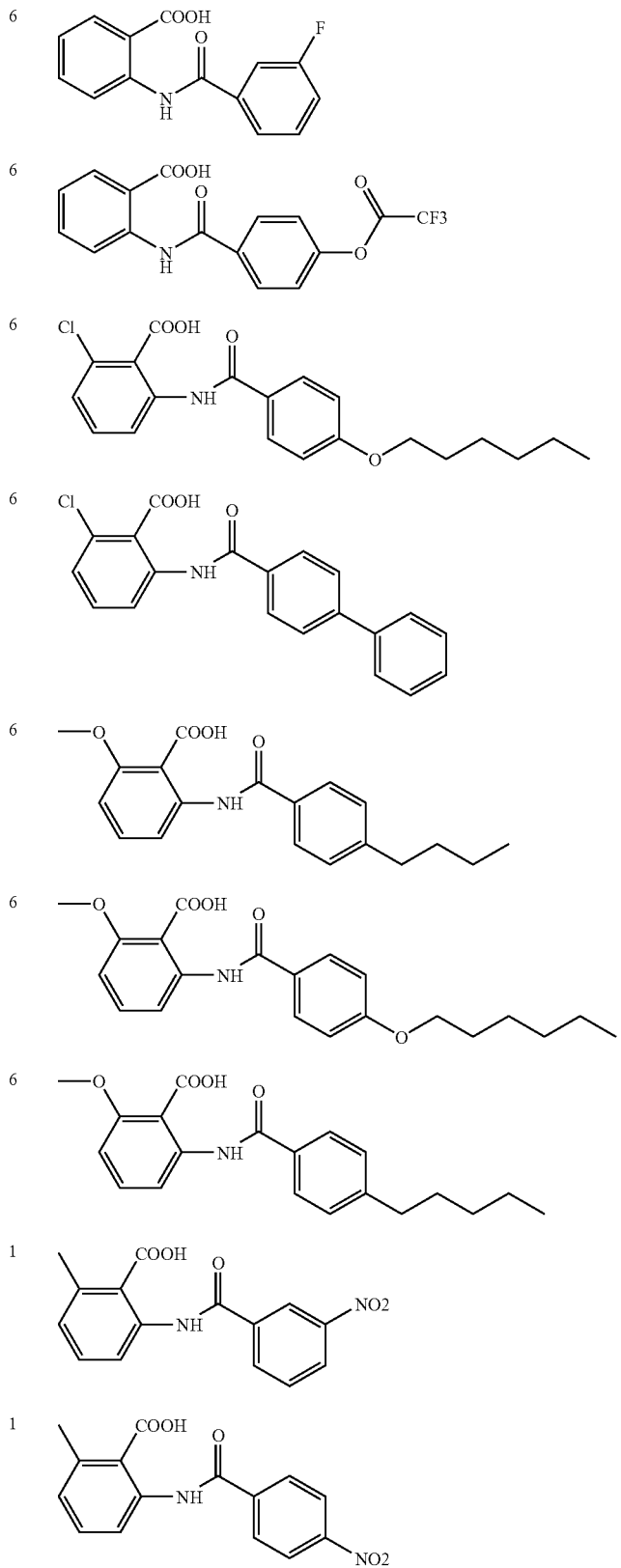 |
| 6 | |
| 6 | |
| 6 | |
| 6 | |
| 6 | |
| 6 | |
| 1 | |
| 1 | |

TABLE I-continued
| scheme | Compound of the present invention |
|---|---|
| 6 | 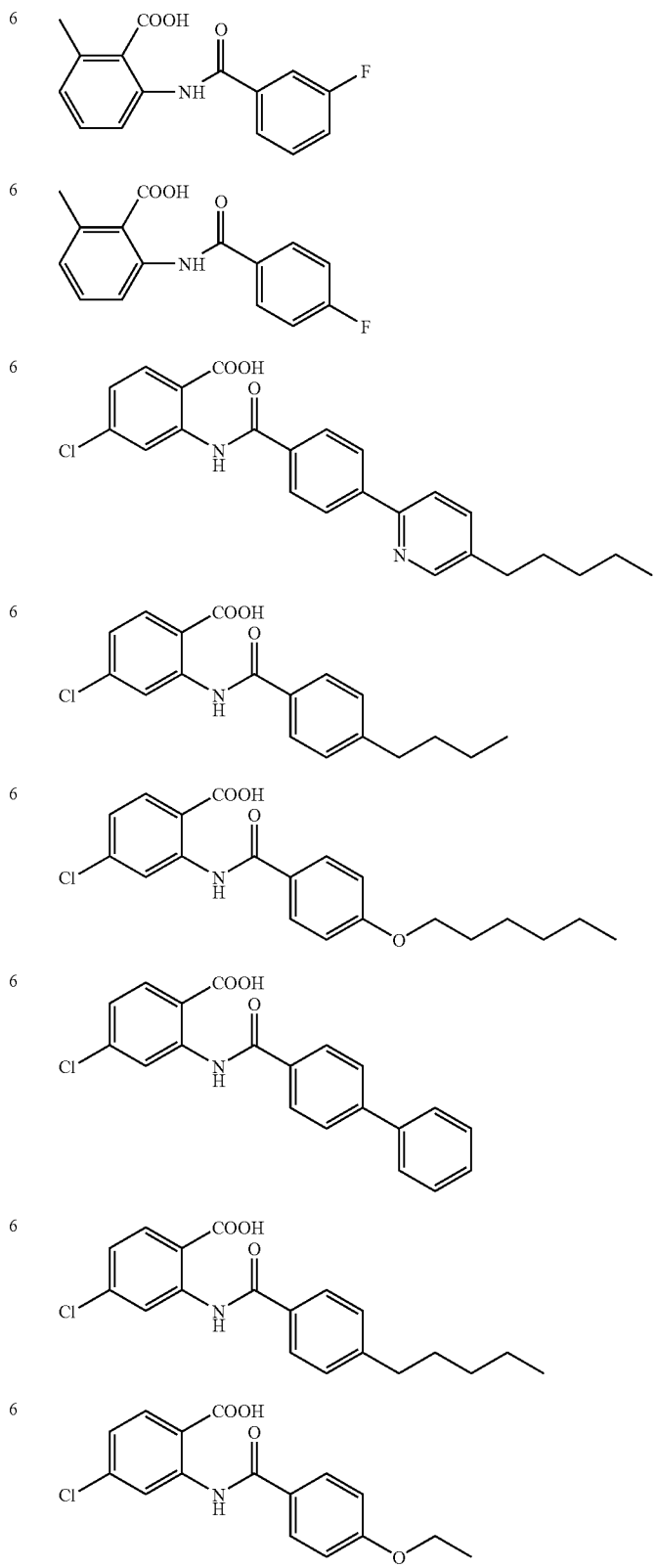 |
| 6 | |
| 6 | |
| 6 | |
| 6 | |
| 6 | |
| 6 | |
| 6 | |

TABLE I-continued
| scheme | Compound of the present invention |
|---|---|
| 6 | 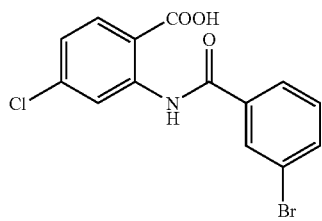 |
| 2 | 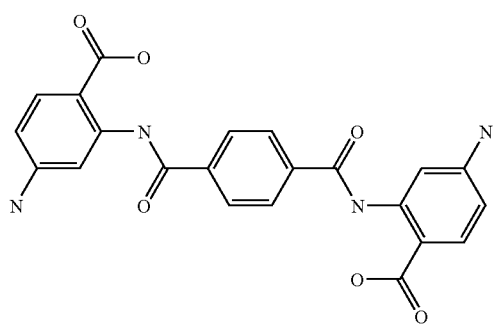 |
| 2 | 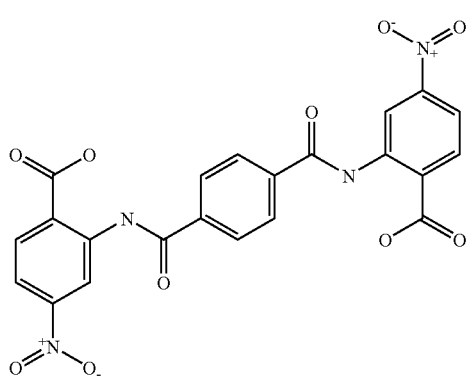 |
| 6 | 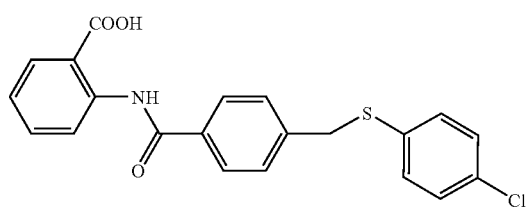 |
| 3 | 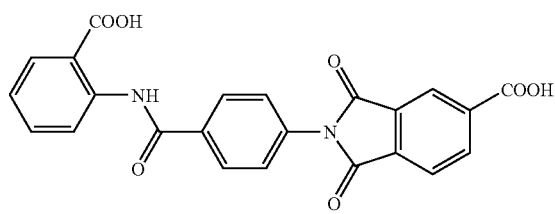 |
| 3 | 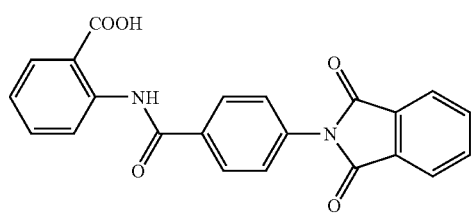 |

TABLE I-continued
| scheme | Compound of the present invention |
|---|---|
| 3 | 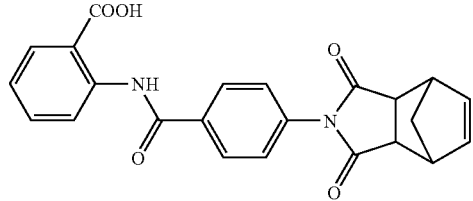 |
| 6 | 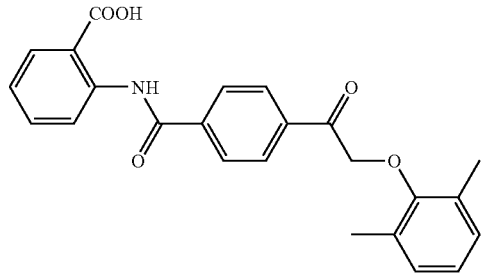 |
| 1 | 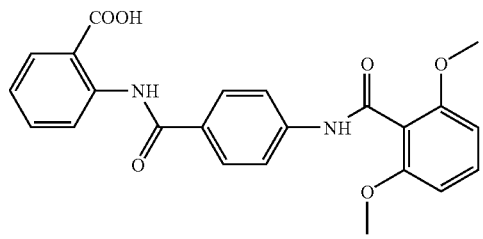 |
| 1 | 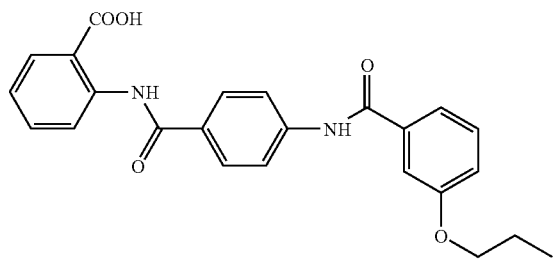 |
| 3 | 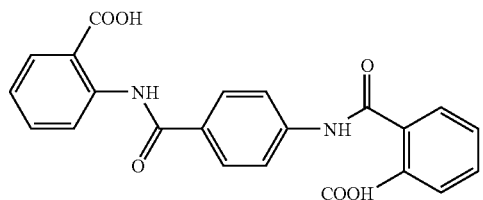 |
| 4 | 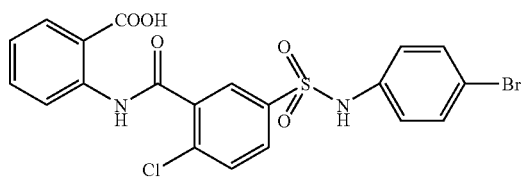 |
| 4 | 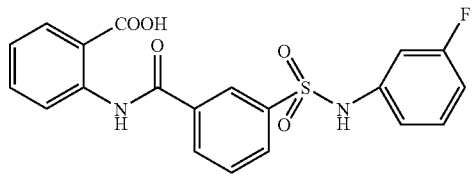 |

TABLE I-continued
| scheme | Compound of the present invention |
|---|---|
| 4 | 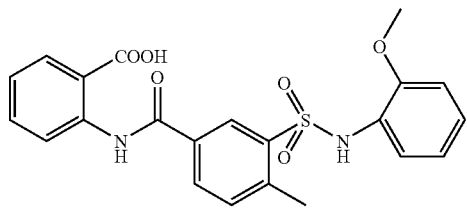 |
| 4 | 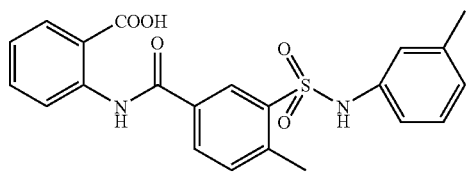 |
| 4 | 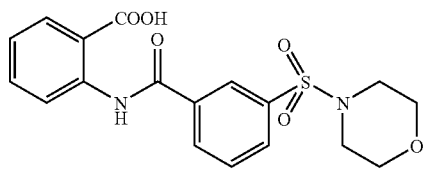 |
| 5 | 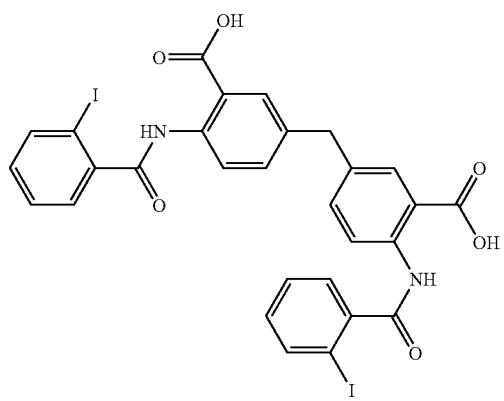 |
| 5 | 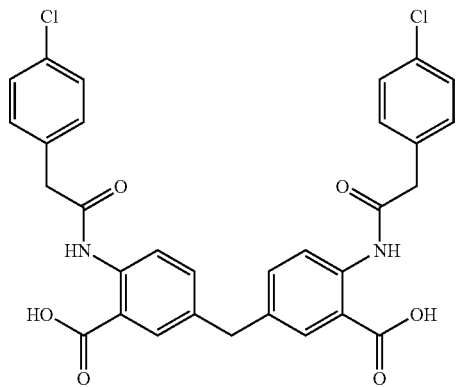 |

TABLE I-continued
| scheme | Compound of the present invention |
| --- | --- |
| 5 | 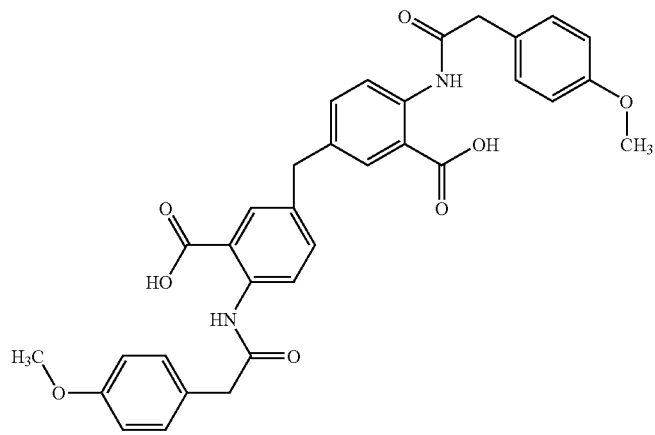 |
| 5 | 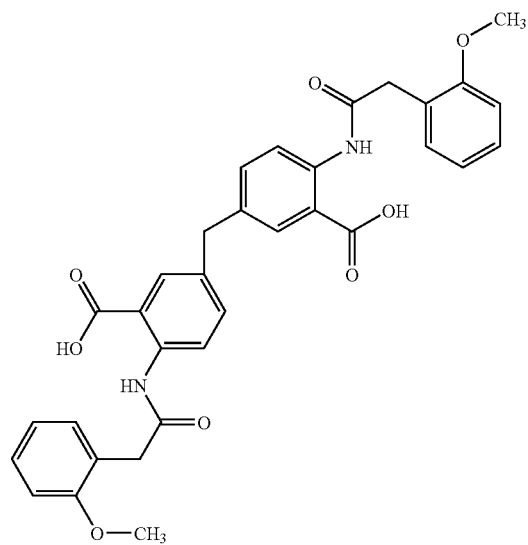 |
| 5 | 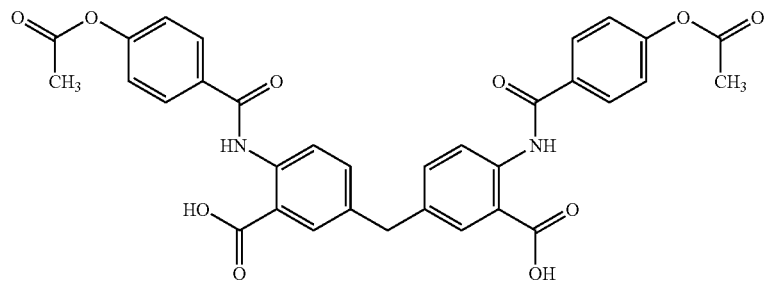 |

TABLE I-continued
| scheme | Compound of the present invention |
|---|---|
| 5 | 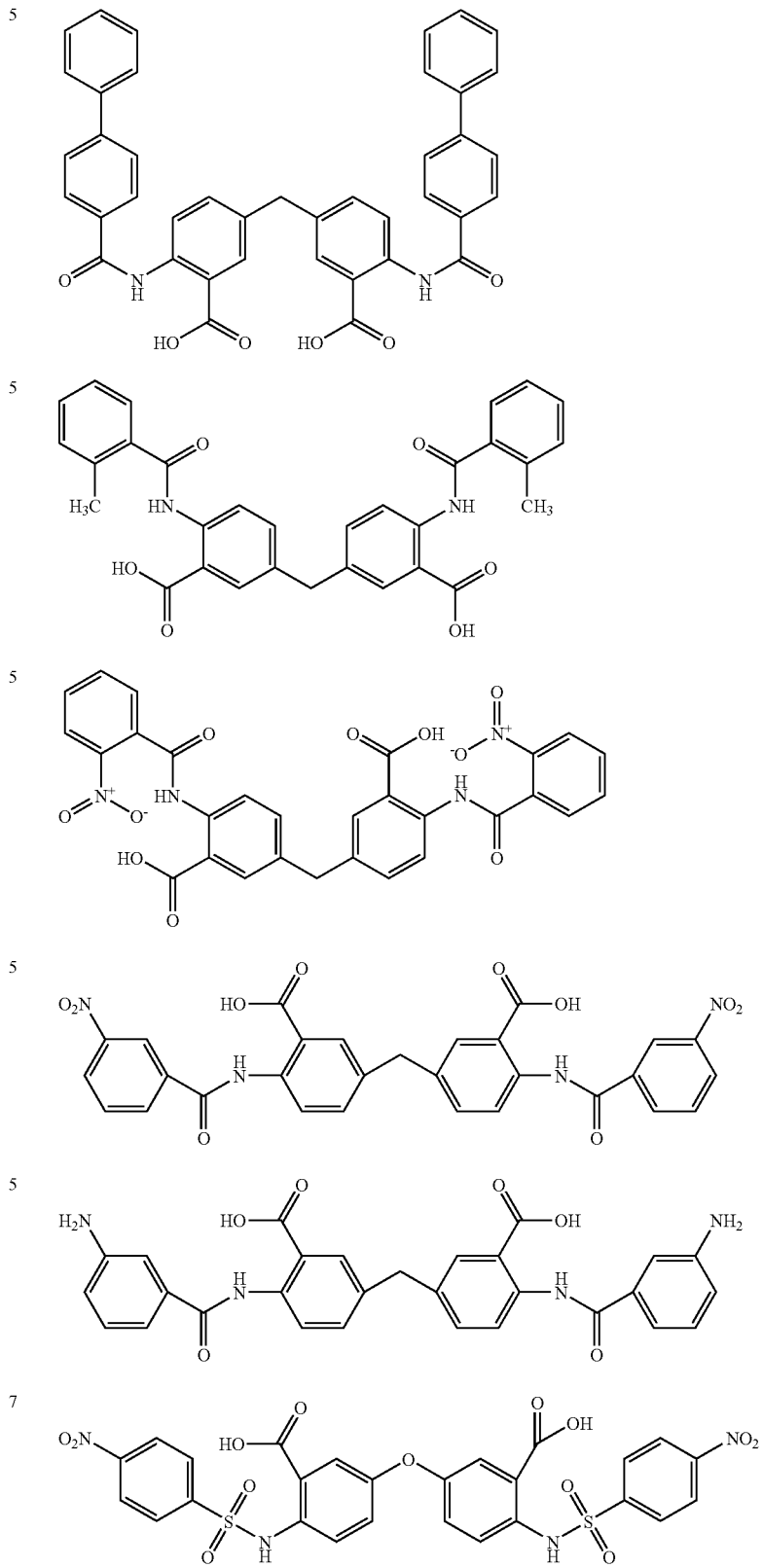 |
| 5 | |
| 5 | |
| 5 | |
| 5 | |
| 7 | |

TABLE I-continued
| scheme | Compound of the present invention |
|---|---|
| 7 | 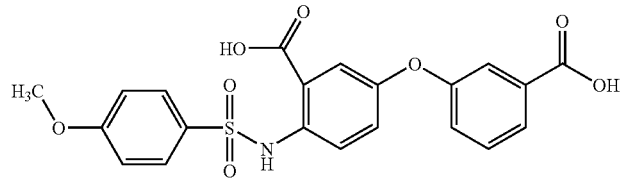 |
| 7 | 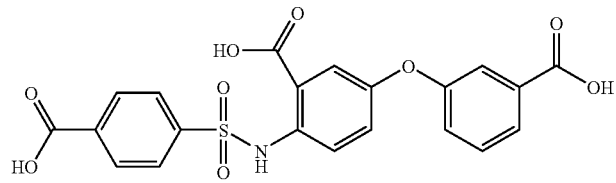 |
| 7 | 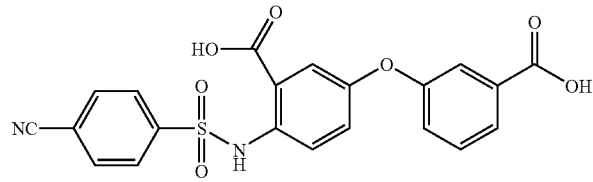 |
| 7 | 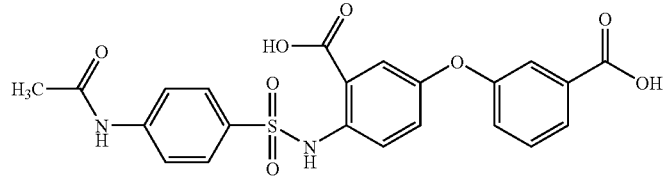 |
| 7 | 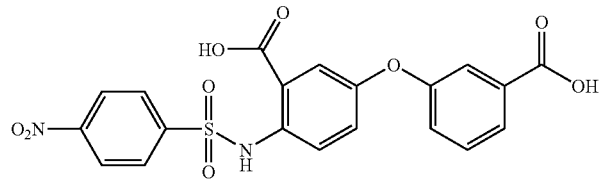 |
| 7 | 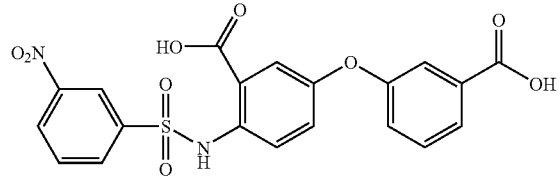 |
| 7 | 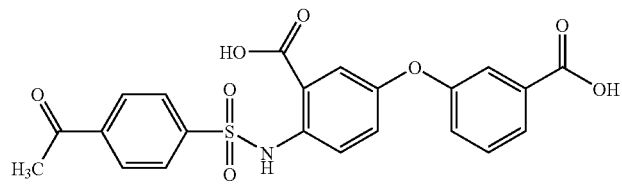 |

TABLE I-continued
| scheme | Compound of the present invention |
|---|---|
| 7 | 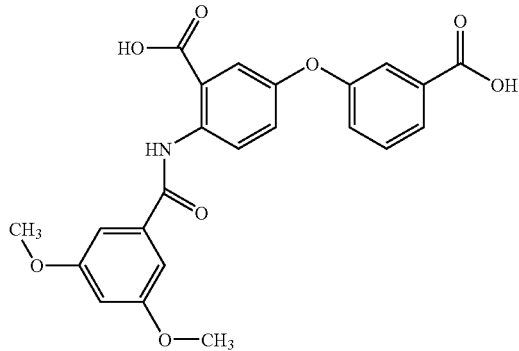 |
| 7 | 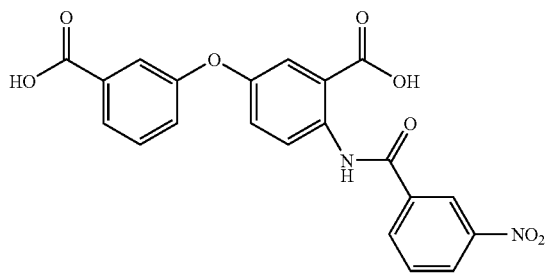 |
| 7 | 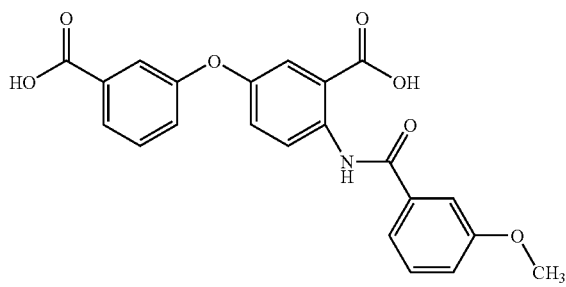 |
| 7 | 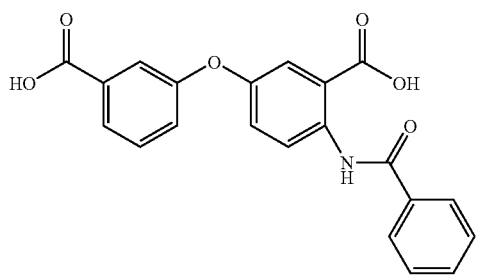 |
| 7 | 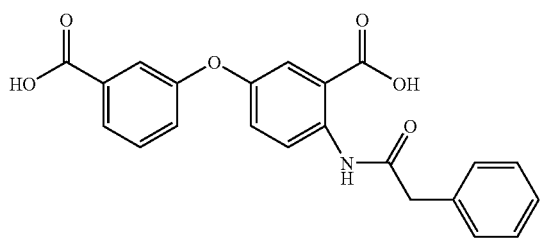 |

TABLE I-continued
| scheme | Compound of the present invention |
|---|---|
| 7 | 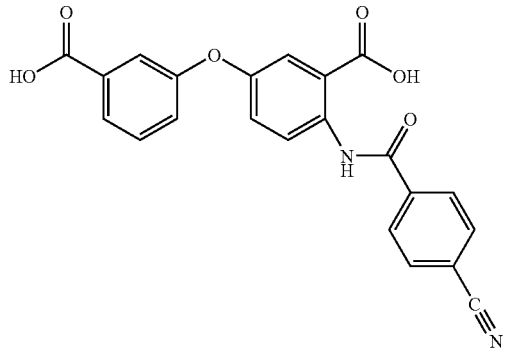 |
| 7 | 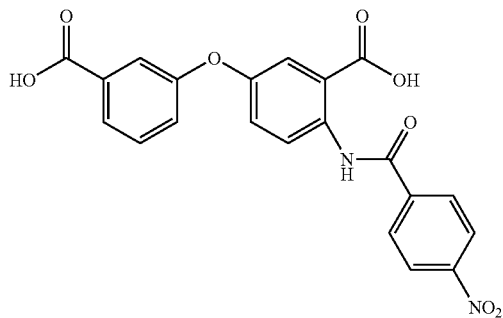 |
| 7 | 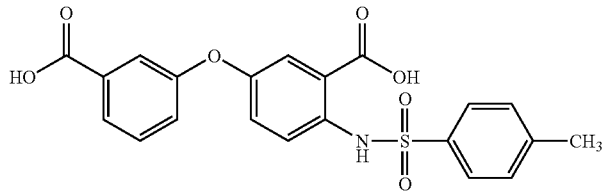 |
| 7 | 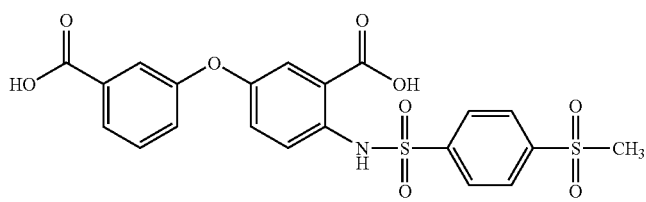 |
| 7 | 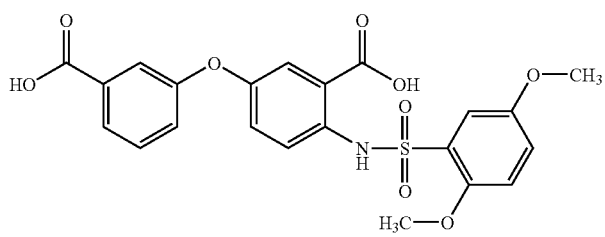 |
| 7 | 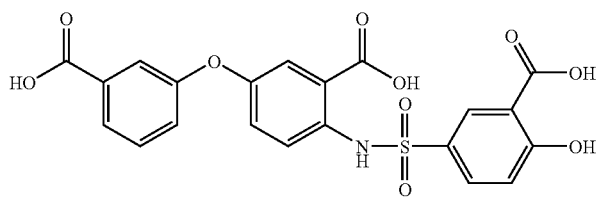 |

TABLE I-continued
| scheme | Compound of the present invention |
|---|---|
| 7 | |
| 7 | |
| 7 | |
| 7 | |
| 7 | |
| 7 | |
| 7 | |
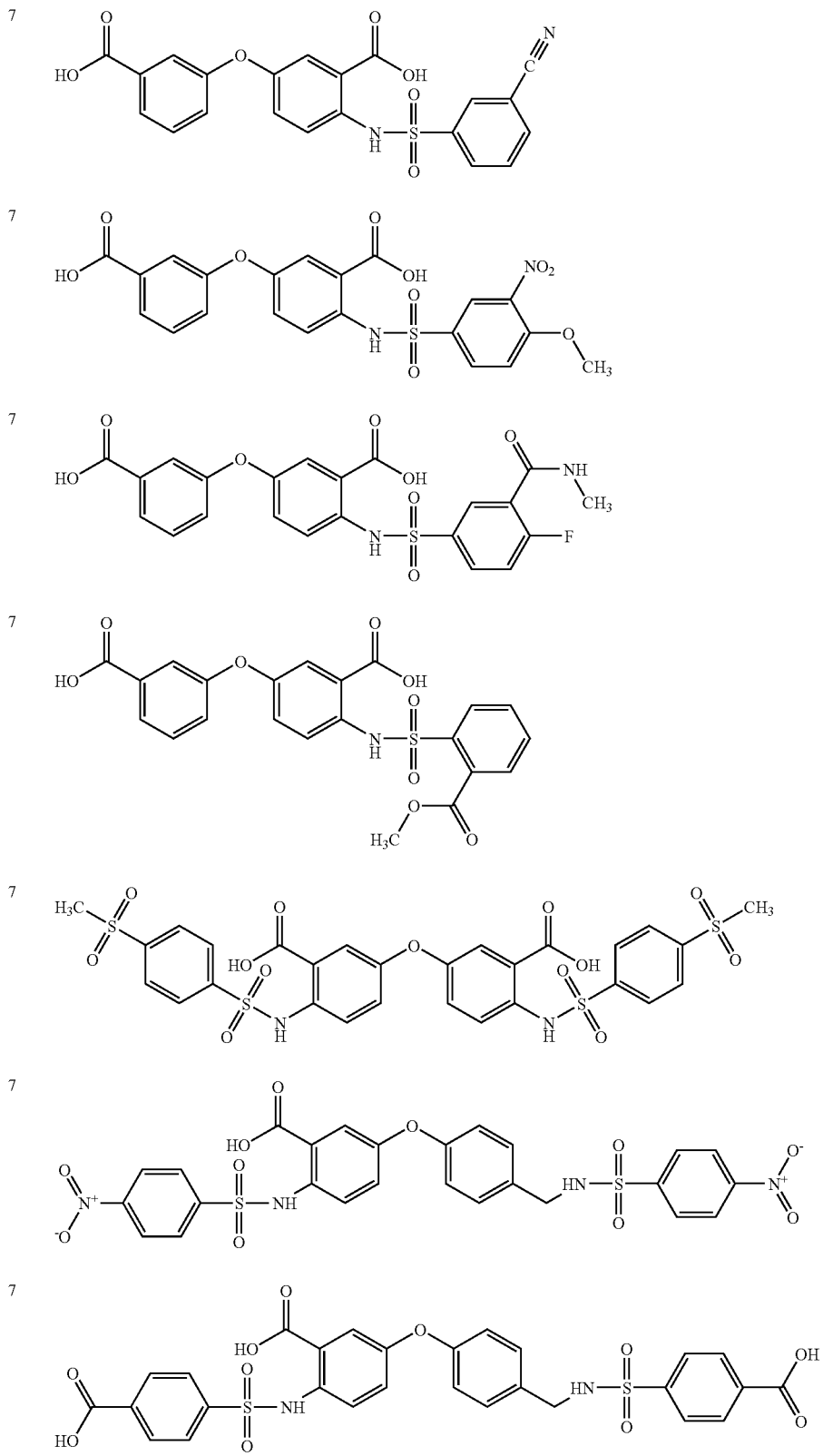

TABLE I-continued
| scheme | Compound of the present invention |
|---|---|
| 7 | 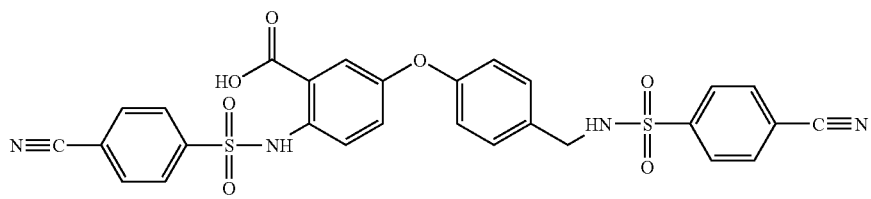 |
| 7 | 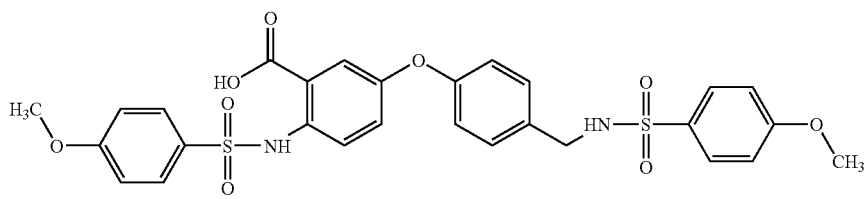 |
| 7 | 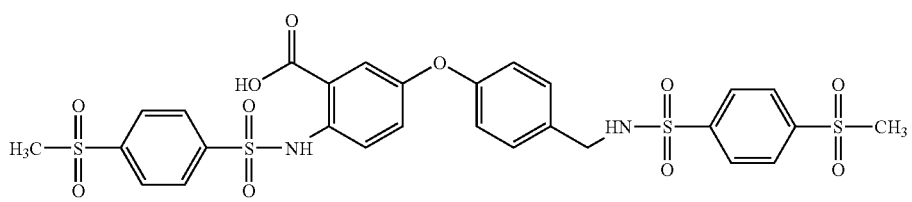 |
| 7 | 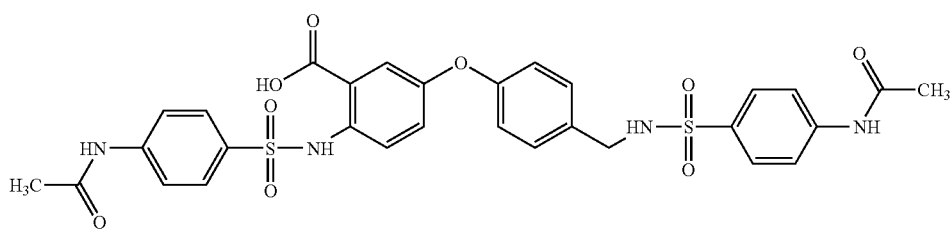 |
| 7 | 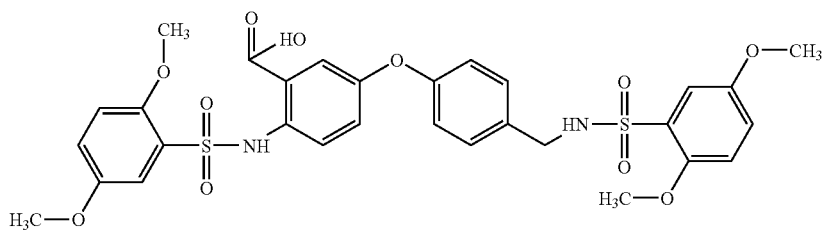 |
| 7 | 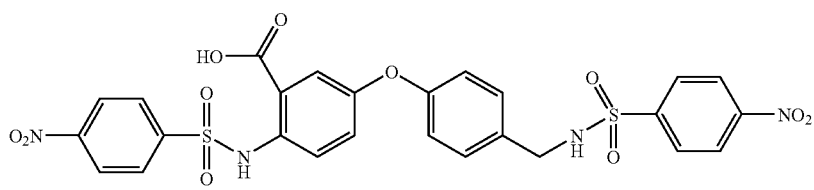 |
| 7 | 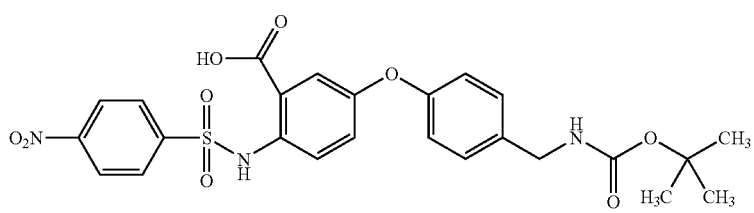 |

TABLE I-continued
| scheme | Compound of the present invention |
|---|---|
| 7 | 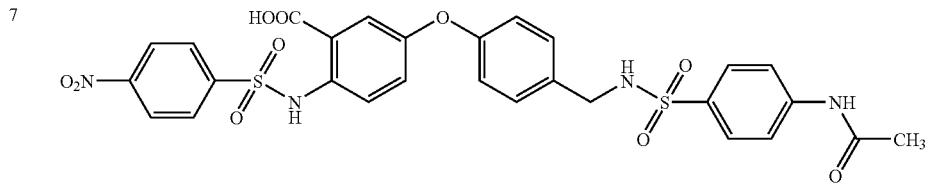 |
| 7 | 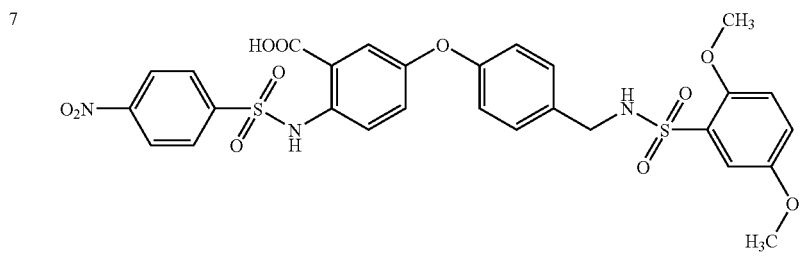 |
| 7 | 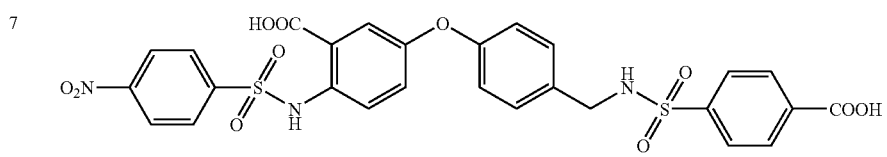 |
| 7 | 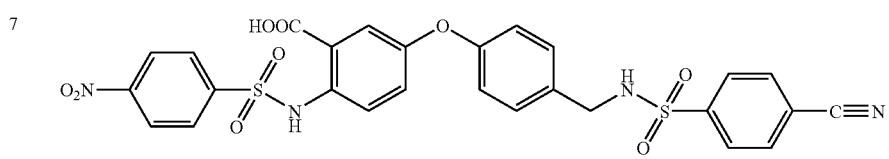 |
| 7 | 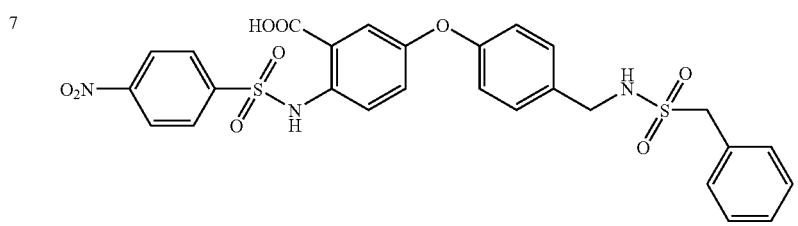 |
| 7 | 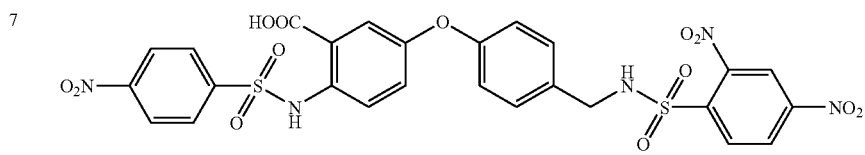 |
| 7 | 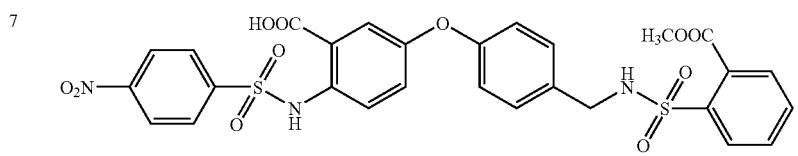 |
| 7 | 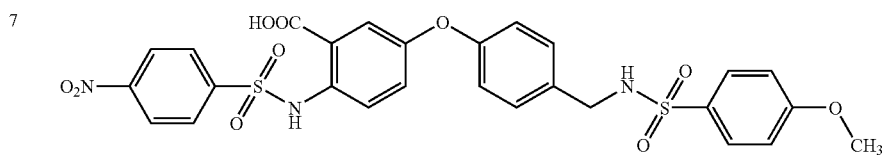 |

TABLE I-continued
| scheme | Compound of the present invention |
|---|---|
| 7 | 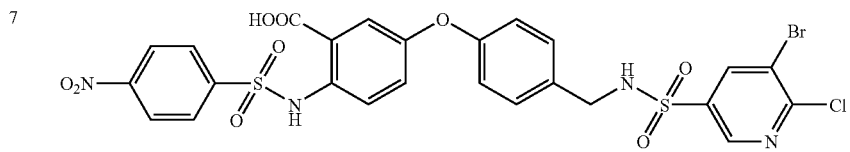 |
| 7 | 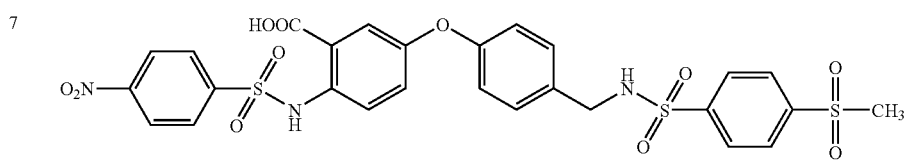 |
| 7 | 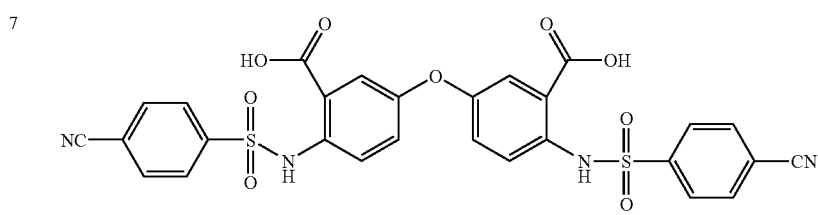 |
| 7 | 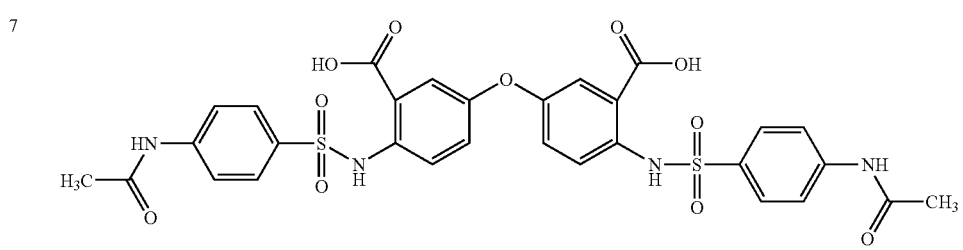 |
| 7 | 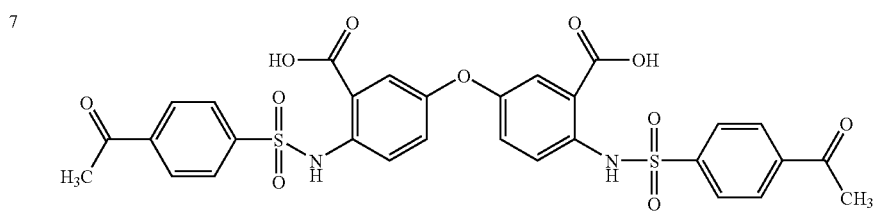 |
| 7 | 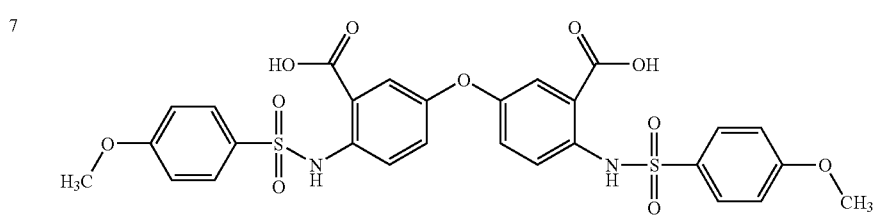 |
| 7 | 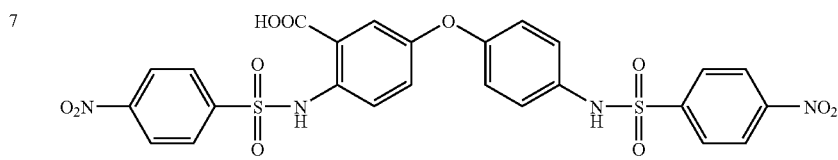 |
| 7 | 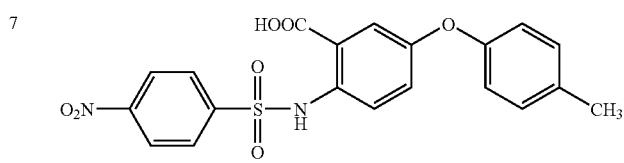 |

TABLE I-continued
| scheme | Compound of the present invention |
|---|---|
| 7 | 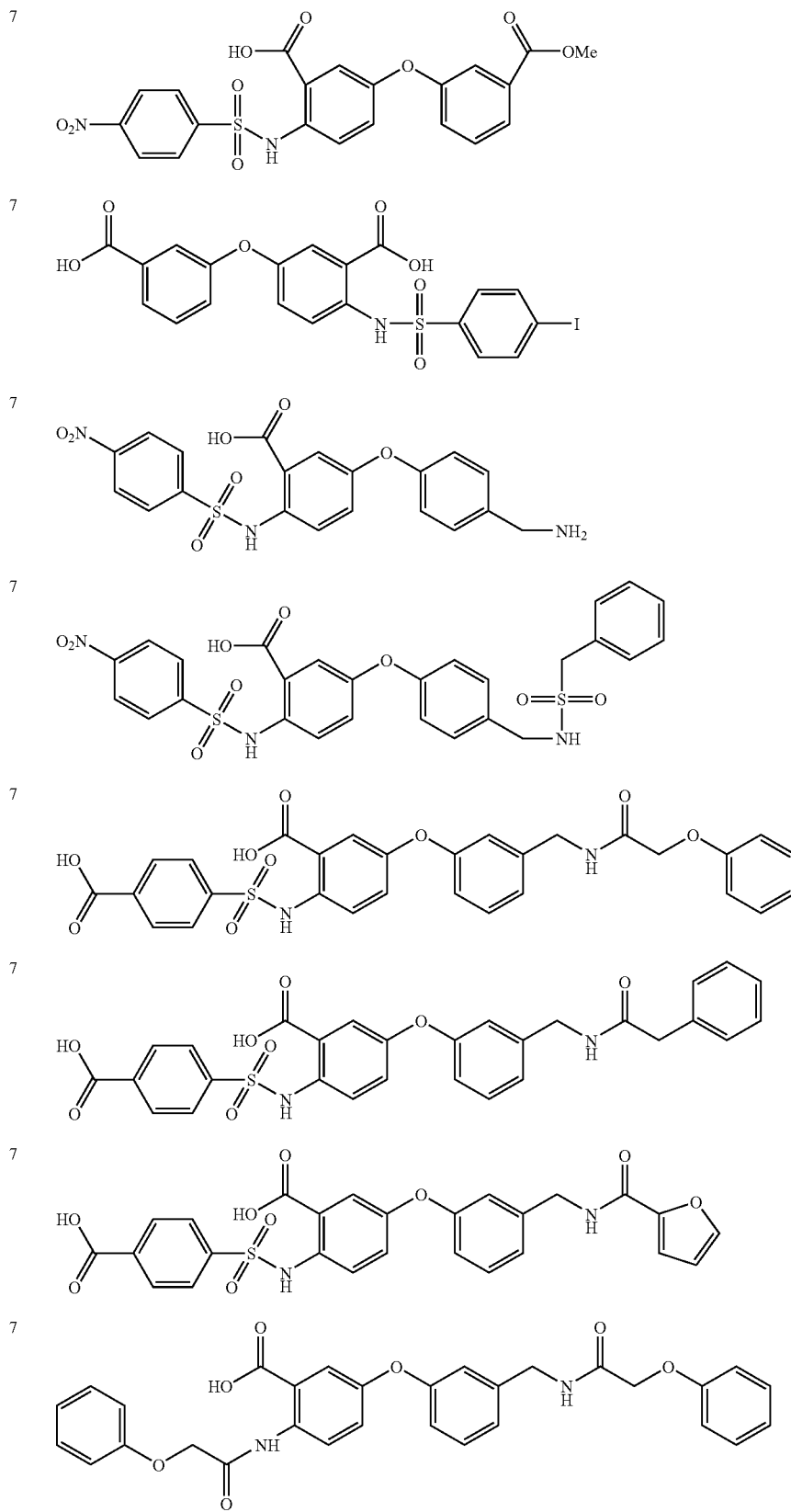 |
| 7 | |
| 7 | |
| 7 | |
| 7 | |
| 7 | |
| 7 | |
| 7 | |

TABLE I-continued
| scheme | Compound of the present invention |
|---|---|
| 7 | 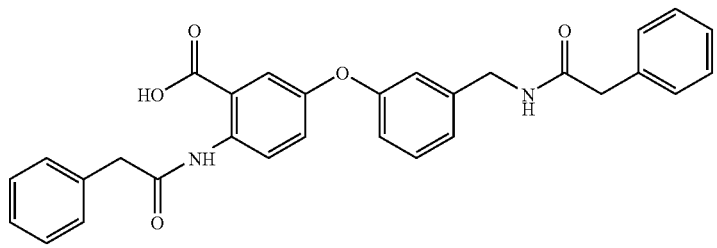 |
| 1 | 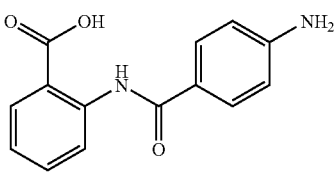 |
| 1 | 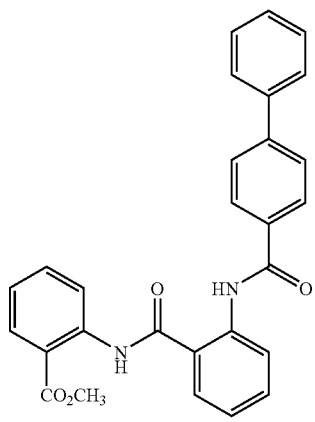 |
| 1 | 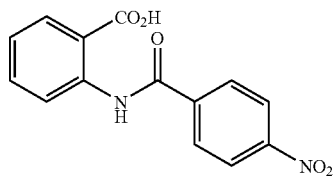 |
| 1 | 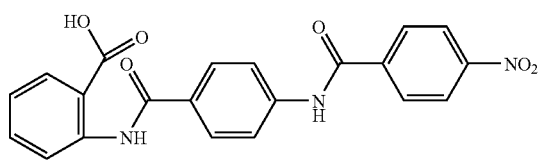 |
| 6 | 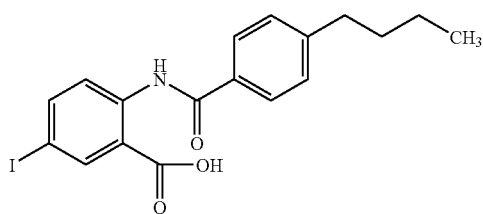 |

TABLE I-continued
| scheme | Compound of the present invention |
|---|---|
| 7 | 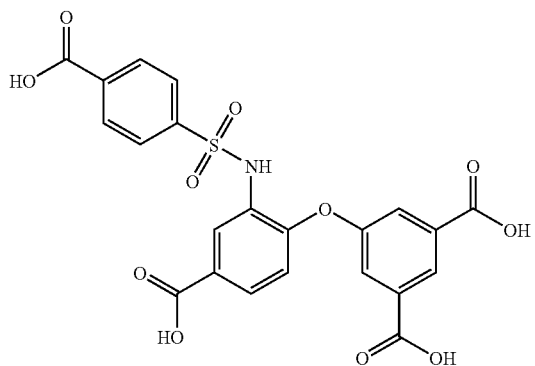 |
| 7 | 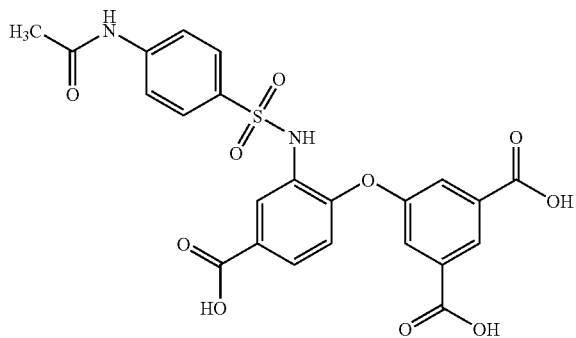 |
| 7 | 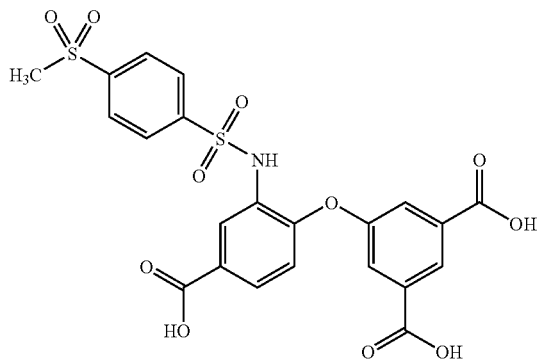 |
| 7 | 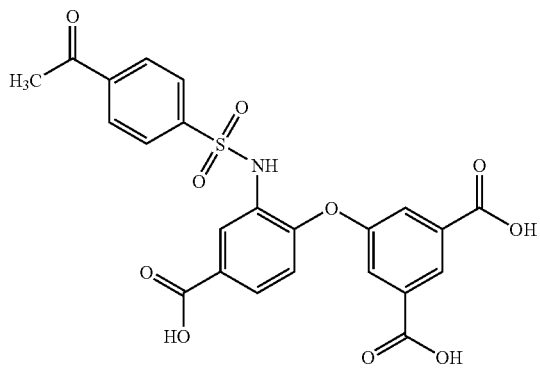 |

TABLE I-continued
| scheme | Compound of the present invention |
|---|---|
| 6 | 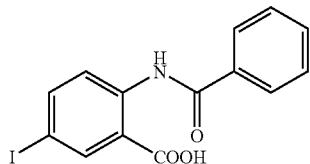 |
| 6 | 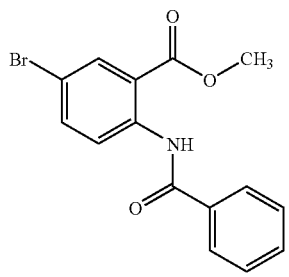 |
| 6 | 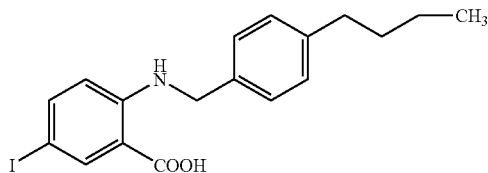 |
| 6 | 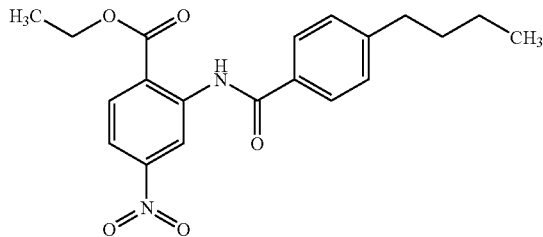 |
| 6 | 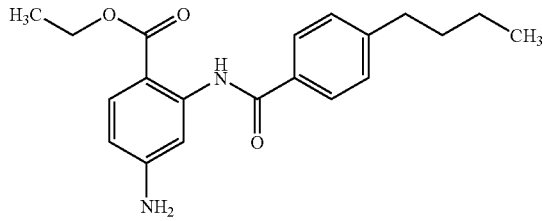 |
| 6 | 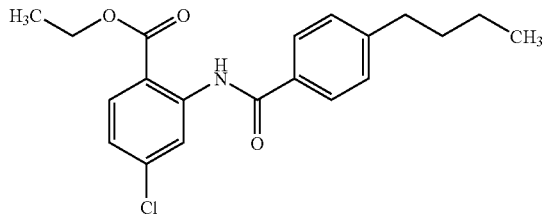 |

TABLE I-continued

| scheme | Compound of the present invention |
|---|---|
| 7 | 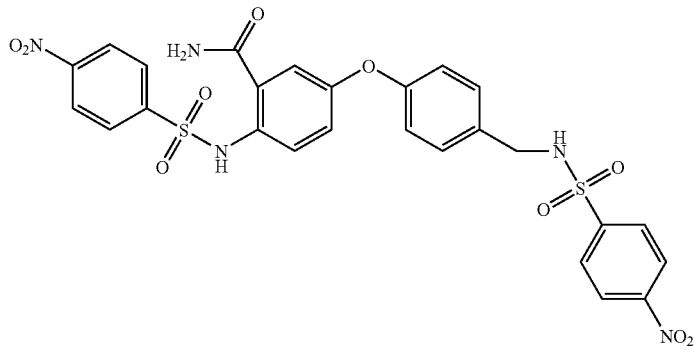 |
| 7 | 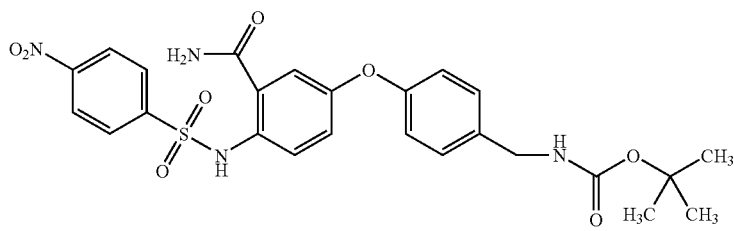 |
| 6 |  |

The compounds of the present invention can thus be used in animals, preferably in mammals, and in particular in humans as pharmaceuticals per se, in mixtures with one another or in the form of pharmaceutical preparations.

Furthermore, the present invention relates to pharmaceutical preparations which as active constituents contain an effective dose of at least one of the compounds in addition to customary pharmaceutically innocuous excipients and auxiliaries. The pharmaceutical preparations normally contain 0.1 to 90% by weight of the compound. The pharmaceutical preparations can be prepared in a manner known per se to one of skill in the art. For this purpose, at least one of a compound of the present invention, together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain a compound according to the invention can be administered orally, parenterally, e.g., intravenously, rectally, by inhalation, or topically, the preferred administration being dependent on the individual case, e.g., the particular course of the disorder to be treated. Oral administration is preferred.

The person skilled in the art is familiar on the basis of his expert knowledge with the auxiliaries which are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

The compounds of the present invention are useful in the treatment of individuals infected by HIV and for the prophylaxis of these individuals. In general, the compounds of the present invention may be useful in the treatment of warm-blooded animals infected with viruses whose existence is mediated by, or depends upon, the integrase enzyme. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV and other pathogenic retroviruses, such as HIV-1. Consequently, the compounds of the present invention can be used in the manufacture of a medicament useful for treating conditions associated with HIV and other pathogenic retroviruses.

In a preferred embodiment, the invention relates to the use of the compounds of the present invention or any subgroup thereof in the manufacture of a medicament for treating or combating infection or disease associated with retrovirus infection in a mammal, such as HIV-1 infection. Thus, the invention also relates to a method of treating a retroviral infection, or a disease associated with retrovirus infection comprising administering to a mammal in need thereof an effective amount of the compounds or a subgroup thereof.

In another preferred embodiment, the present invention relates to the use of the compounds or any subgroup thereof in the manufacture of a medicament for inhibiting entry of a retrovirus in a mammal infected with said retrovirus, in particular HIV-1 retrovirus.

In another preferred embodiment, the present invention relates to the use of the compounds or any subgroup thereof in the manufacture of a medicament for inhibiting retroviral entry, in particular the fusion mechanism.

The compounds of the present invention may also find use in inhibiting ex vivo samples containing HIV or expected to be exposed to HIV. Hence, the present compounds may be used to inhibit HIV present in a body fluid sample which contains or is suspected to contain or be exposed to HIV.

Also, the combination of an antiretroviral compound and a compound of the present invention can be used as a medicine. Thus, the present invention also relates to a product containing (a) a compound of the present invention, and (b) another antiretroviral compound, as a combined preparation for simultaneous, separate or sequential use in treatment of retroviral infections. Thus, to combat or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4; fusion inhibitors, such as, for example, T20, T1249, SHC—C; co-receptor binding inhibitors, such as, for example, AMD 3100 (Bicyclams), TAK 779; RT inhibitors, such as, for example, foscarnet and prodrugs; nucleoside RTIs, such as, for example, AZT, 3TC, DDC, DDI, D4T, Abacavir, FTC, DAPD, dOTC; nucleotide RTIs, such as, for example, PMEA, PMPA, tenofovir; NNRTIs, such as, for example, nevirapine, delavirdine, efavirenz, 8 and 9-Cl TIBO (tivirapine), loviride, TMC-125, TMC-120, MKC-442, UC 781, Capravirine, DPC 961, DPC963, DPC082, DPC083, calanolide A, SJ-3366, TSAO, 4"-deaminated TSAO; RNAse H inhibitors, such as, for example, SP1093V, PD126338; TAT inhibitors, such as, for example, RO-5-3335, K12, K37; integrase inhibitors, such as, for example, L 708906, L 731988; protease inhibitors, such as, for example, amprenavir, ritonavir, nelfinavir, saquinavir, indinavir, lopinavir, lasinavir, BMS 232632, BMS 186316, DPC 681, DPC 684, tipranavir, AG1776, DMP 450, L 756425, PD178390, PNU 140135; glycosylation inhibitors, such as, for example, castanospermine, deoxynojirimycine.

The combination may provide a synergistic effect, whereby viral infectivity and its associated symptoms may be prevented, substantially reduced, or eliminated completely.

The compounds of the present invention may also be administered in combination with immunomodulators (e.g., bropirimine, anti-human alpha interferon antibody, IL-2, methionine enkephalin, interferon alpha, and naltrexone) or with antibiotics (e.g., pentamidine isothiorate) to ameliorate, combat, or eliminate HIV infection and its symptoms.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefor such as solubilizers, emulsifiers or further auxiliaries, are brought into solution, suspension, or emulsion. The compounds can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds in pharmaceutical compositions, it can be advantageous to employ α-, β- or γ-cyclo-dextrins or their derivatives. Also co-solvents such as alcohols may improve the solubility and/or the stability of the compounds in pharmaceutical compositions. In the preparation of aqueous compositions, addition salts of the subject compounds are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with alkyl, particularly methyl, ethyl or isopropyl, e.g. randomly methylated β-CD; hydroxyalkyl, particularly hydroxyethyl, hydroxypropyl or hydroxybutyl; carboxyalkyl, particularly carboxymethyl or carboxyethyl; alkylcarbonyl, particularly acetyl; alkyloxycarbonylalkyl or carboxy-alkyloxyalkyl, particularly carboxymethoxypropyl or carboxyethoxypropyl; alkylcarbonyloxyalkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifungal active ingredients, they are equally interesting for formulating the compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavors.

Other convenient ways to enhance the solubility of the compounds of the present invention in pharmaceutical compositions are described in WO-94/05263, PCT application No. PCT/EP98/01773, EP-A499299 and WO 97/44014, all incorporated herein by reference.

More in particular, the present compounds may be formulated in a pharmaceutical composition comprising a therapeutically effective amount of particles consisting of a solid dispersion comprising (a) a compound of the present invention, and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion is referred to as "a solid solution". Solid solutions are preferred physical systems because the components therein are usually readily bio-available to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the compounds of this invention are incorporated in hydrophilic polymers and applying this mixture as a coat film over many small beads, thus yielding a composition with good bioavailability which can conveniently be manufactured and which is suitable for preparing pharmaceutical dosage forms for oral administration.

Said beads comprise (a) a central, rounded or spherical core, (b) a coating film of a hydrophilic polymer and an antiretroviral agent and (c) a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

Another aspect of the present invention concerns a kit or container comprising a compound of the present invention, in an amount effective for use as a standard or reagent in a test or assay for determining the ability of a potential pharmaceutical to inhibit HIV entry, HIV growth, or both. This aspect of the invention may find its use in pharmaceutical research programs.

The compounds of the present invention can be used in phenotypic resistance monitoring assays, such as known recombinant assays, in the clinical management of resistance developing diseases such as HIV. A particularly useful resistance monitoring system is a recombinant assay known as the Antivirogram™. The Antivirogram™ is a highly automated, high throughput, second generation, recombinant assay that can measure susceptibility, especially viral susceptibility, to the compounds of the present invention. (Hertogs K, de Bethune M P, Miller V et al. Antimicrob Agents Chemother, 1998; 42(2): 269-276, incorporated by reference).

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight and individual responsiveness of the human or animal to be treated and on whether the therapy is acute or prophylactic. Customarily, the daily dose of a compound of the present invention, in the case of administration to a patient approximately 75 kg in weight is 1 mg to 1 g, preferably 3 mg to 0.5 g. The dose can be administered in the form of an individual dose, or divided into several, e.g. two, three, or four, individual doses.

EXAMPLES

Example 1

Scheme 5: Preparation of Compounds of Formula (III)

To a mixture of 0.5 g of compound 5-A in 25 ml of THF, at room temperature, was added water 5 ml and sodium carbonate 745 mg. The mixture was stirred for 30 min and compounds 5-B, 2.2 equivalents in THF (5 ml) were added drop wise. The reaction mixture was stirred for 3 hours and filtered to get compounds 5-C. Compound 5-C was dissolved in water and the solution was acidified with a concentrated hydrochloric acid solution until pH=3 and extracted with ethyl acetate. The organic layer was separated, dried over $MgSO_4$ and evaporated to yield 514 mg (54%) of compound 5-D.

organic layer was separated, dried over MgSO$_4$ and evaporated to yield 503 mg (32%) of compound 6-C.

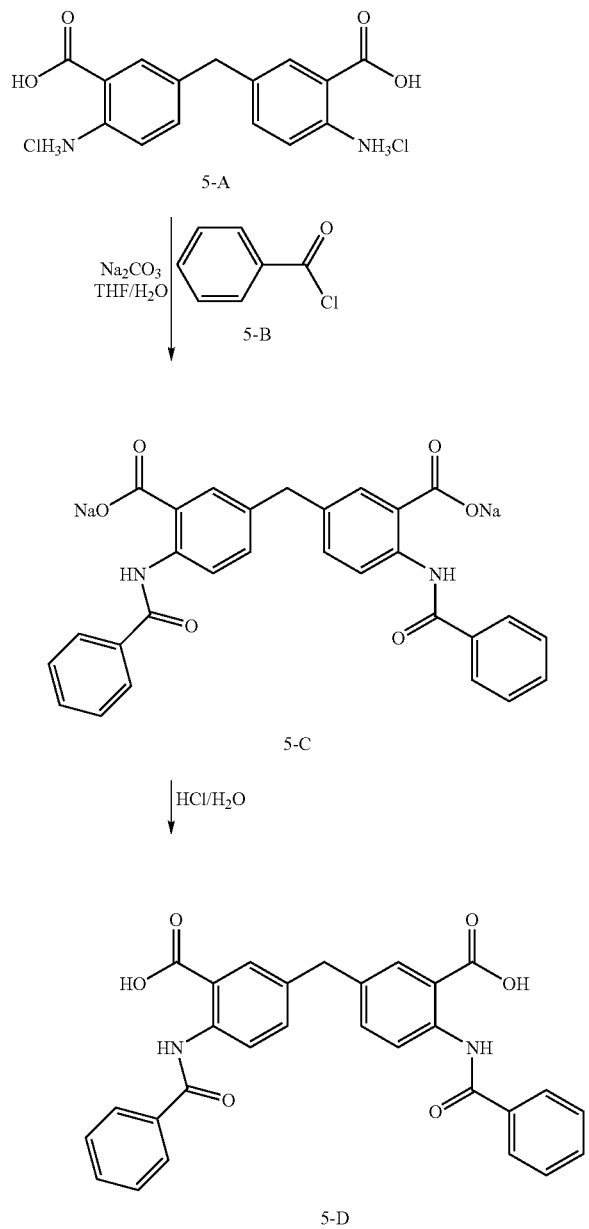

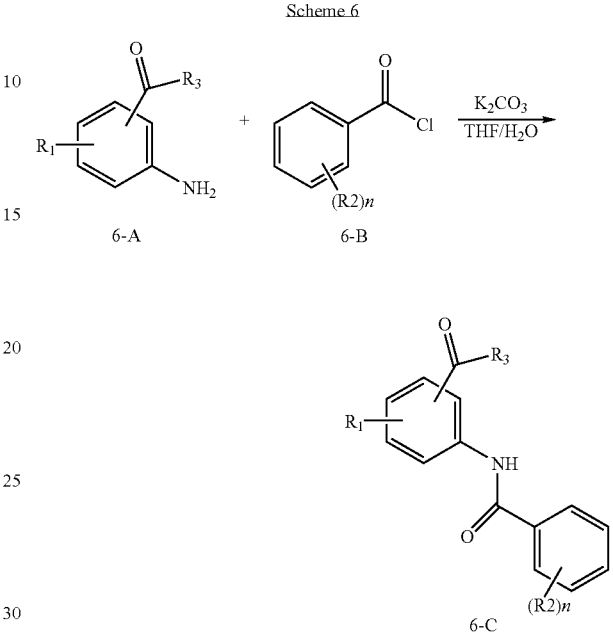

Example 3

Scheme 7: Preparation of Compounds of Formula (III)

To a mixture of 1.5 g of compound 7-A (R1=—CN) in 25 ml of DMF, at room temperature, was added potassium carbonate 5.2 g (3 equivalent). The mixture was stirred for 30 min at 80° C. and compound 7-B 2.33 g, was added. The reaction mixture was stirred for 12 hours at 140° C. The reaction was monitored by TLC, when starting material was consumed, the mixture was then allowed to warm up to RT and water was added. The solution was acidified by adding a solution of hydrochloric acid until pH=3. The product was extracted with ethyl acetate. The organic layer was separated, dried over MgSO$_4$ and evaporated to yield 3 g (83%) of compound 7-C.

Example 2

Scheme 6: Preparation of Compounds of Formula (I)

To a mixture of 1 g of compound 6-A in 30 ml of THF, at room temperature, was added water 10 ml and potassium carbonate 1.57 g. The mixture was stirred for 30 min and compounds 6-B, 1.1 equivalents were added drop wise. The reaction mixture was stirred for 3 hours and acidified with a concentrated hydrochloric acid solution until pH=3. The resulting solution was extracted with ethyl acetate. The

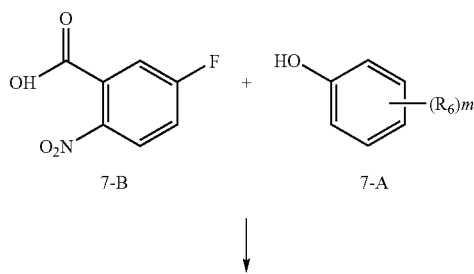

-continued

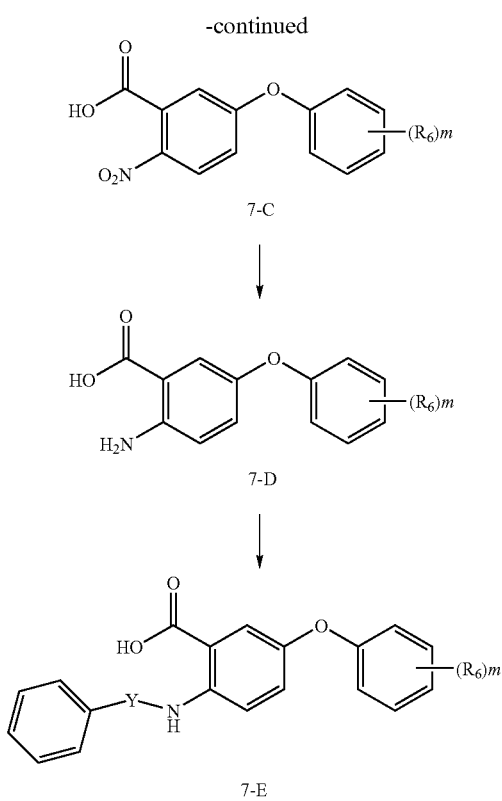

7-C

↓

7-D

↓

7-E

A mixture of compound 7-C 6.2 g was dissolved in methanol and a catalytic amount of palladium on carbon was added (when R1=—CN some amount of thiophene were needed to poison the catalyst). The mixture was stirred at RT under hydrogen. After 4 hours the mixture was filtered and the solvent was removed. Compound 7-D 5 g (R1=mCO2H) was isolated as a white powder.

To a mixture of 1.8 g of compound 7-D in 50 ml of THF, at room temperature, was added water 15 ml and sodium carbonate 3.4 g. The mixture was stirred for 30 min and acyl chlorides or sulfonylchlorides were added, 1.1 equivalents. The reaction mixture was stirred for 12 hours. The reaction mixture was acidified with a concentrated hydrochloric acid solution until pH=3 and extracted with ethyl acetate. The organic layer was separated, dried over MgSO₄ and evaporated to yield compound 7-E.

Example 4

The compounds in Table 1 exemplify the present invention and were tested in an HIV entry assay where the percentage of binding inhibition effected by 100 micromolar of compound was measured. The inhibition of the binding affinity of IQN17 and Alexa-C28 in the presence of the different compounds (i.e. the ability of the compounds to displace Alexa-C28 from a binding site on IQN-17) was measured by capillary zone electrophoresis. Capillary electrophoresis experiments were conducted on a Beckman Coulter P/ACE System MDQ and a Spectrumedix 9610HTS. The capillaries used in the Beckman Coulter had an inner diameter of 75 µm, 50 cm of effective length, and inner surface of fused silica. Separations were conducted with an applied voltage of 30 kV. The capillaries used in the Spectrumedix 9610HTS had an inner diameter of 50 µm, effective length of 50 cm, and an inner surface of fused silica. Separations were conducted with an applied voltage of 13 kV. Separation buffer was 20 mM sodium borate, pH=8.5.

IQN17 is a soluble, non-aggregating trimeric peptide model of the pocket-forming residues of gp41, and a highly soluble GCN4-based, isoleucine coiled-coil peptide. C28 is a helical polypeptide consisting of a segment derived from the C-terminal helix of gp41 enclosing residues 628655.

Compounds were dissolved in binding buffer. Binding was measured in solutions of Alexa-C28 and IQN-17. Buffer, IQN-17, a compound of the invention, and Alexa-C28 were mixed in that order. DMSO was added to bring the concentration in the final solution to 5% by volume. The compounds were allowed to bind for at least one hour prior to measurement by CZE. The areas of the Alexa-C28 peaks at a constant concentration of IQN-17 and varying concentrations of compounds was analyzed in comparison to the area of Alexa-C28 in the absence of compound and IQN-17. The percentage of binding inhibition exhibited by the compounds ranged from 3.5% to 175%.

The invention claimed is:

1. A compound having the formula (III),

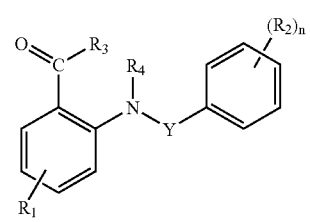

a N-oxide form, a stereochemical isomer, racemic mixture, salt, prodrug, or ester, wherein R¹ represents a radical of formula (II),

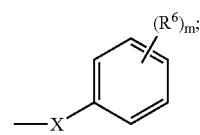

R² is bromo, chloro, alkyl, alkyloxy, or haloalkyl, wherein said R² radicals are located in compound of formula (III), respective from the moiety Y, at meta, para, and meta and para positions;

n is 1;

Y is —C(=O)—, or —S(=O)₂—;

R³ is hydroxy or alkyloxy;

R⁴ is hydrogen or alkyl;

X is —CH₂—;

each R⁶ is independently R⁷—C(=O)—, R⁸—S(=O)₂—NH—, or R⁸—C(=O)—NH—, said substitutents R⁶ are adjacent; in meta and para positions, or in ortho and meta positions;

R[7] is hydroxy or alkyloxy;

R[8] is aryl substituted with halogen, bromo, chloro, alkyl, alkyloxy haloalkyl, alkenyl, or alkynyl, said substituents in meta or para position respective from the point of attachment of said aryl group; and m is 2.

2. A pharmaceutical composition containing a compound as claimed in claim 1 and one or more pharmaceutically acceptable excipients.

3. The compound 3'-methylene-bis(6-((4-methylphenyl)sulfonylamino)-benzoic acid), or its N-oxide form, salt, stereoisomeric form, racemic mixture, prodrug, or ester.

4. The compound having the following structure:

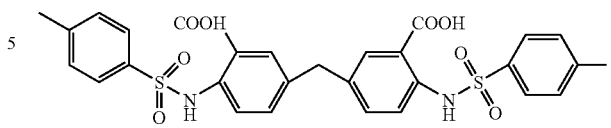

according to claim 3.